(12) United States Patent
Boudreaux

(10) Patent No.: US 7,838,232 B2
(45) Date of Patent: Nov. 23, 2010

(54) CAIDAG-GEF1 GENE MUTATIONS ASSOCIATED WITH THROMBOPATHY IN CANINES

(75) Inventor: Mary K. Boudreaux, Auburn, AL (US)

(73) Assignee: Auburn University, Auburn, AL (US)

( * ) Notice: Subject to any disclaimer, the term of this patent is extended or adjusted under 35 U.S.C. 154(b) by 377 days.

(21) Appl. No.: 11/874,557

(22) Filed: Oct. 18, 2007

(65) Prior Publication Data

US 2009/0035760 A1 Feb. 5, 2009

Related U.S. Application Data

(60) Provisional application No. 60/853,401, filed on Oct. 19, 2006, provisional application No. 60/881,771, filed on Jan. 22, 2007.

(51) Int. Cl.
*C07H 21/04* (2006.01)
*C12Q 1/68* (2006.01)
(52) U.S. Cl. .................... 435/6; 435/91.1; 435/91.2; 536/23.1; 536/24.3
(58) Field of Classification Search ............ None
See application file for complete search history.

(56) References Cited

PUBLICATIONS

James L. Catalfamo et al; Thrombin Receptor-Activating Peptides Unlike Thrombimn are Insufficient for Platelet Activation in Most Species Abstract; Thromb Haemost vol. 69; 1993; pp. 1195.
Mary K. Boudreaux et al; Calcium-Diacylglycerol Guanine Nucleotide Exchange Factor I gene mutations associated with loss of function in canine platelets; Translation Res. 150; 2007; pp. 81-92.
Jan Schultress et al; Rap1GAP2 is a new GTPase-activating protein of Rap1 expressed in human platelets; 2005 by The American Society of Hematology; pp. 3185-3192.
Sanford J. Shattil and Peter J. Newman; Integrins: dynamic scaffolds for adhesion and signaling in platelets; Blood, Sep. 15, 2004; vol. 104, No. 6, pp. 1606-1615.
Wolfgang Bergmeier et al; Mice lacking the signaling molecule CaIDAG-GEFI represent a model for leukocyte adhesion deficiency type III; The Journal of Clinical Investigation; vol. 117, No. 6, Jun. 2007; pp. 1699-1707.
Ronit Pasvolsky et al; A LAD-III syndrome is associated with defective expression of the Rap-1 activator CaIDAG-GEFI in lymphocytes, neutrophils, and platelets; The Rockefeller University Press; vol. 204, No. 7, Jul. 9, 2007; pp. 1571-1582.
Magdalena Chrzanowska-Wodnicka et al; Rap1b is required for normal platelet function and hemostasis in mice; The Journal of Clinical Investigation; vol. 115; No. 3, Mar. 2005; pp. 680-687.
Donna Woulfe et al; Activation of Rap1B by Gi Family Members in Platelets; The Journal of Biological Chemistry; vol. 277; No. 26; Issue of Jun. 28, 2002; pp. 23382-23390.
Amuro Torti and Eduardo G. Lapentina; Role of rap1B and p21ras GTPase-activating protein in the regulation of phospholipase C-gamma1 in human platelets; Proc. Natl. Acad. Sci. USA; vol. 89, Aug. 1992; pp. 7796-7800.
Barbara Franke, Jan-Willem N.Akkerman and Johannes L.Bos; Rapid Ca2+ -mediated activation of Rap1 in human platelets; The EMBO Journal, vol. 16, No. 2, 1997, pp. 252-259.
Thomas H. Fischer et al; rap1B, a cAMP-dependent Protein Kinase Substrate, Associates with the Platelet Cytoskeleton; The Journal of Biological Chemistry; vol. 265, No. 32, Nov. 15, 1990; pp. 19405-19408.
Eduardo G. Lapetina et al; A ras-related protein is phosphorylated and translocated by agonists that increase cAMP levels in human platelets; Proc. Natl. Acad. Sci. USA; vol. 86; May 1989; pp. 3131-3134.
Johannes L.Bos; All in the family? New insights and questions regarding interconnectivity of Ras, Rap1 and Ral; The EMBO Journal, vol. 17; No. 23; 1998; pp. 6776-6782.
Bruno Bernardi et al; The small GTPase Rap1b regulates the cross talk between platelet integrin alpha1 beta1 and integrin alphaIIb beta3; Blood, vol. 107, No. 7; Apr. 1, 2006; pp. 2728-2735.
Paolo Lova et al; A Gi-dependent Pathway Is Required for Activation of the Small GTPase Rap1B in Human Platelets; The Journal of Biological Chemistry; vol. 277; No. 14, Issue of Apr. 5, 2002; pp. 12009-12015.
Adam J. Dupuy et al; Activation of the Rap1 Guanine Nucleotide Exchange Gene, CaIDAG-Gef I, in BXH-2 Murine Myeloid Leukemia; The Journal of Biological Chemistry; vol. 276; No. 15; Issue of Apr. 13, 2001; pp. 11804-11811.
Shigeko Yamashita et al; CaIDAG-GEFIII Activation of Ras, R-Ras, and Rap1; The Journal of Biological Chemistry; vol. 275; No. 33; Issue of Aug. 18, 2000; pp. 25488-25493.
Masamichi Shiraga et al; Primary Megakaryocytes Reveal a Role for Transcription Factor NF-E2 in Integrin alphaIIB beta3 Signaling; The Journal of Cell Biology; vol. 147; No. 7; Dec. 27, 1999; pp. 1419-1429.
Hiroaki Kawasaki et al; A Rap guanine neucleotide exchange factor enriched highly in the basal ganglia; Proc. Natl. Acad. Sci. USA, vol. 95; Oct. 1998; pp. 13278-13283.
Barbara Franke et al; Sequential Regulation of the Small GTPase Rap1 in Human Platelets; Molecular and Cellular Biology; vol. 20, No. 3; Feb. 2000; pp. 779-785.
Patricia A. Gentry et al; An Inherited Platelet Function Defect in a Simmental Crossbred Herd; Can J Vet Res 1997; vol. 61; pp. 128-133.
Gene P. Searcy and Lyall Petrie; Clinical and laboratory findings of a bleeding disorder in eight Simmental cattle; Can Vet J; vol. 31; Feb. 1990; pp. 101-103.
Gene P. Searcy et al; Preliminary Studies of a Platelet Function Disorder in Simmental Cattle; Can J Vet Res; 1990; vol. 54, pp. 394-396.
Barbara A. Steficek et al; Hemorrhagic diathesis associated with a hereditary platelet disorder in Simmental cattle; J Vet Diagn Invest 5; 1993; pp. 202-207.
I.B. Johnstone and F. Lotz; An Inherited Platelet Function Defect in Basset Hounds; Can. Vet. J. vol. 20; Aug. 1979; pp. 211-215.
James L. Catalfamo et al; Defective Platelet-Fibrinogen Interaction in Hereditary Canine Thrombopathia; Blood, vol. 67; No. 6; Jun. 1986; pp. 1568-1577.

(Continued)

*Primary Examiner*—Jeanine A Goldberg
(74) *Attorney, Agent, or Firm*—Andrus, Sceales, Starke & Sawall, LLP

(57) ABSTRACT

The present invention relates to methods and compositions for detecting mutations associated with thrombopathy. In particular, the invention relates to methods and composition for detecting mutations in the CalDAG-GEF1 gene that are associated with thrombopathy.

19 Claims, 6 Drawing Sheets

OTHER PUBLICATIONS

Marjory B. Brooks et al; A hereditary bleeding disorder of dogs caused by a lack of platelet procoagulant activity; Blood, vol. 99; No. 7, Apr. 2002; pp. 2434-2441.

Koji Eto et al; Magakaryocytes derived from embryonic stem cells implicate CaIDAG-GEFI in integrin signaling; PNAS; vol. 99; No. 20; Oct. 1, 2002; pp. 12819-12824.

Bruno Bernardi et al; The small GTPase Rap1b regulates the cross talk between platelet integrin alpha2 beta1 and integrin alphaIIB beta3; Blood, vol. 107; No. 7; Apr. 1, 2006; pp. 2728-2735.

D.L. Lipscomb et al; Two Genetic Defects in alphaIIb Are Associated with Type I Glanzmann's Thrombasthenia in a Great Pyrenees Dog: A 14-base Inse6rtion in Exon 13 and Splicing Defect of Intron 13; Vet Pathol; vol. 37; 2000; pp. 581-588.

M.K. Boudreaux and D.L. Lipscomb; Clinical, Biochemical, and Molecular Aspects of Glanzmann's Therombasthenia in Humans and Dogs; Vet Pathol; vol. 38; 2001; pp. 249-260.

P.W. Christopherson et al; Characterization of the cDNA Encoding alphaIIb and beta3 in Normal Horses and Two Horses with Glanzmann Thrombasthenia; Vet Pathol; vol. 43; 2006; pp. 78-82.

Alessandra Bertoni et al; Relationships between Rap1b, Affinity Modulation of Integrin alphaIIB beta3, and the Actin Cytoskeleton; The Journal of Biological Chemistry; vol. 277; No. 28, Jul. 12, 2002; pp. 25715-25721.

Reuben J. Mapletoft et al; A study of the inheritance of a bleeding disorder in Simmental cattle; Can Vet J; vol. 41; Oct. 2000; pp. 791-793.

A. Koneti Rao and Jagadeesh Gabbeta; Congenital Disorders of Platelet Signal Transduction; Arterioscler Thromb Vasc Biol.; vol. 20; 2000; pp. 285-289.

Jill R. Crittenden et al; CaIDAG-GEFI integrates signaling for platelet aggregation and thrombus formation; Nature Medicine; vol. 10; No. 9; Sep. 2004; pp. 982-986.

Kimberly L. Dodge-Kafka and Michael S. Kapiloff; The mAKAP signaling complex: Integration of cAMP, calcium, and MAP kinase signaling pathways; European Journal of Cell Biology; pp. 594-602.

M.K. Boudreaux et al; A Platelet Activation-specific Monoclonal Antibody that Recognizes a Receptor-induced Binding Site on Canine Fibrinogen; Department of Pathobiology, College of Veterinary Medicine, Auburn University, Auburn, AL; pp. 419-427.

M.F. McConnell et al; Circumvention of the Basset Hound Hereditary Thrombopathy by Platelet Activation with Phorbal Myristate Acetate; Platelets; vol. 6, No. 3, 1995; pp. 131-145.

Lidija Covic et al; Biphasic Kinetics of Activation and Signaling for PAR1 and PAR4 Thrombin Receptors in Platelets; Biochemistry 2000, 39; pp. 5458-5467.

Claudia K. Derian et al; Species Differences in Platelet Responses to Thrombin and SFLLRN, Receptor-Mediate Calcium Mobilization and Aggregation, and Regulation by Protein Kinases; Thrombosis Research; vol. 78, No. 6, 1995; pp. 505-519.

Mary K. Boudreaux et al; Identification of an Intrinsic Platelet Function Defect in Spitz Dogs; Journal of Veterinary Internal Medicine; vol. 8, No. 2; Mar.-Apr. 1994; pp. 93-98.

Barbara A. Steficek et al; A Primary Platelet Disorder of Consanguineous Simmental Cattle; Thrombosis Research 72; 1993; pp. 145-153.

Gene P. Searcy et al; Platelets from Bleeding Simmental Cattle Mobilize Calcium, Phosphorylate Myosin Light Chain and Bind Normal Numbers of Fibrinogen Molecules but Have Abnormal Cytoskeletal Assembly and Aggregation in Response to ADP; Thrombosis and Haemostasis; vol. 71, No. 2, 1994; pp. 240-246.

Christine B. Navarre et al; Platelet Function Defect in a 5-Day-Old Simmental Calf; Journal of Veterinary Internal Medicine; vol. 9, No. 4; Jul.-Aug. 1995; pp. 283-285.

Mony M. Frojmovic et al; Platelets from Bleeding Simmental Cattle Have a Long Delay n both ADP-activated Experssion of GpIIB-IIIA Receptors and Fibrinogen-dependent Platelet Aggregation; Thrombosis and Haemostasis; vol. 76, No. 6; 1996; pp. 1047-1052.

Wayne R. Patterson et al; Absent Platelet Aggregation with Normal Fibrinogen Binding in Basset Hound Hereditary Thrombopathy; Thrombosis and Haemostasis; vol. 62, No. 3; 1989; pp. 1011-1015.

Mary K. Boudreaux et al; Impaired cAMP Metabolism Associated with Abnormal Function of Thrombopathic Canine Platelets; Biochemical and Biophysical Research Communications; vol. 140, No. 2; Oct. 30, 1986; pp. 595-601.

Mary K. Boudreaux et al; Evidence for Regulatory Control of Canine Platelet Phosphodiesterase; Biochemical and Biophysical Research Communications; vol. 140, No. 2; Oct. 30, 1986; pp. 589-594.

M.K. Boudreaux et al; Type I Glanzmann's Thrombasthenia in a Great Pyrenees Dog; Vet. Pathol. 33; 1996; pp. 503-511.

Lawrence A. Quilliam et al; A Growing Family of Guanine Nucleotide Exchange Factors Is Responsible for Activation of Ras-Family GTPases; Progress in Nucleic Acid Research and Molecular Biology; vol. 71; 2002; pp. 391-445.

Figure 1

Primers used to amplify cDNA segments:

| | | | |
|---|---|---|---|
| Pre Exon 1f | GAGGCCCAGAGTGCAGCGTGA | forward | |
| Exon 6r | GTGATGACCAGGGCACGCTGA | reverse | 718 bp |
| Exon 6f | CTCATGGCTGCACCGTGGACA | forward | |
| Exon 11r | GTCCCCAAAGGCGCTGAGGTA | reverse | 846 bp |
| Exon 11f | GGGGATGGCCACATCTCACAG | forward | |
| UTRr | GCTTCCTGCTCTGGTCCAAGT | reverse | 565 bp |

Primers used to amplify DNA segments:

| | | | |
|---|---|---|---|
| Pre Exon 1f | GAGGCCCAGAGTGCAGCGTGA | forward | |
| Intron 2r | GCTCTAGGAGCGAAGCCCAAT | reverse | 981 bp |
| Intron 2f | CCCTGCAGTCCCAGTCCATGA | forward | |
| Intron 3r | GCCAGTCTGAAGCCTGAGCAA | reverse | 809 bp |
| Intron 2f end | GCCACCCAGGCATCCCAGTTT | forward | |
| Intron 4r | GGTGACAGGGAGCCAGAGGTT | reverse | 708 bp |
| Intron 4f | GCAAAGGGCTCATTGCCCTTG | forward | |
| Intron 5r | CCCTCCAGCTGCCCTTCATTG | reverse | 354 bp |
| Intron 5f | GCCTTTGGTCCAGGGTGGAGT | forward | |
| Intron 7r | CCCAGGGCTTGATGAGGTTCT | reverse | 706 bp |
| Intron 7f | GGGTGTTCCCTTGAGCTCATG | forward | |
| Intron 8r | GAGCCCAGGCTGGATCTCAGT | reverse | 645 bp |
| Intron 8f | GACAGTGGGCTCCTGAGGACA | forward | |
| Exon 11r | GTCCCCAAAGGCGCTGAGGTA | reverse | 909 bp |
| Intron 10f | GGAGAGCCACTCACGTCTGAG | forward | |
| Intron 11r | CCTCTGCCGAGATCATCTGGT | reverse | 334 bp |
| Intron 11af | CAGGAGTGGGGTGAGGATCTT | forward | |
| Intron 13r | GCTGCAAGGTACTTCGCTGCT | reverse | 679 bp |
| Intron 12f | CCGAAAGCACCAGGGTCAGTG | forward | |
| Intron 14r | CTCCCCTCACAGGCCAATACA | reverse | 728 bp |
| Intron 14f | GCATCGAGCCTTCCAGAAGTG | forward | |
| UTRr | GCTTCCTGCTCTGGTCCAAGT | reverse | 565 bp |

Figure 3

Exon 5

```
        151(452)                                                170(509-511)
     [F    D   H   L   E   P   L   E   L   A   E   H   L   T   Y   L   E   Y   R   S   F   C   K   I]   L
D  TTCGACCACCTGGAACCCTTGGAACTAGCAGAGCATCTCACCTACTTAGAGTATCGCTCCTTCTGCAAGATCCTG
B  TTCGACCACCTGGAACCCTTGGAACTAGCAGAGCATCTCACCTACTTAGAGTATCGCTCCTXXXGCAAGATCCTG
S  TTCGAACCACCTGGAACCCTTGGAACTAGCAGAGCATCTCACCTACTTAGAGTATCGCTCCTTCTGCAAGATCCT
L  TTCGACCACCTGGAACCCTTGGAACTAGCAGAGCATCTCACCTACTTAGAGTATCGCTCCTTCTGCAAGATCCTG
M  TTCGACCACCTGGAACCCTTGGAACTAGCAGAGCATCTCACCTACTTAGAGTATCGCTCCTTCTGCAAGATCCTG
C  TTCGACCACCTGGAACCCTTGGAACTAGCAGAGCATCTCACCTACTTAGAGTATCGCTCCTTCTGCAAGATCCTG
```

Exon 6                                         Exon 7

```
     [R   A   L   V   I   T   H   F   V   H   V   A   E     K   L   L   H   L   Q   N   F   N   T   L   M
D  CGTGCCCTGGTCATCACGCACTTTGTCCACGTGGCAGAG  AAGCTGCTTCACTTGCAGAACTTCAACACTCTGATC
B  CGTGCCCTGGTCATCACGCACTTTGTCCACGTGGCAGAG  AAGCTGCTTCACTTGCAGAACTTCAACACTCTGATC
S  GCGTGCCCTGGTCATCACGCACTTTGTCCACGTGGCAGA  GAAGCTGCTTCACTTGCAGAACTTCAACACTCTGAT
L  CGTGCCCTGGTCATCACGCACTTTGTCCACGTGGCAGAG  AAGCTGCTTCACTTGCAGAACTTCAACACTCTGATC
M  CGTGCCCTGGTCATCACGCACTTTGTCCACGTGGCAGAG  AAGCTGCTTCACTTGCAGAACTTCAACACTCTGATC
C  CGTGCCCTGGTCATCACGCACTTTGTCCACGTGGCAGAG  AAGCTGCTTCACTTGCAGAACTTCAACACTCTGATC
```

```
                                                                266(796)
      A   V   V   G   G   L   S   H   S   S   I   S   R   L   K   E   T   H]   S   H   V   S   S   E   T
D  GCCGTGGTCGGAGGCCTGAGCCACAGCTCCATCTCCCGCCTCAAGGAGACTCACAGTCATGTTAGCTCTGAGACC
B  GCCGTGGTCGGAGGCCTGAGCCACAGCTCCATCTCCCGCCTCAAGGAGACTCACAGTCATGTTAGCTCTGAGACC
S  GGCCGTGGTCGGAGGCCTGAGCCACAGCTCCATCTCCCGCCTCAAGGAGACTCACAGTCATGTTAGCTCTGAGAC
L  GCCGTGGTCGGAGGCCTGAGCCACAGCTCCATCTCCCGCCTCAAGGAGACTCACAGTCATGTTAGCTCTGAGACC
M  GCCGTGGTCGGAGGCCTGAGCCACAGCTCCATCTCCCGCCTCAAGGAGACTCACAGTCATGTTAGCTCTGAGACC
C  GCCGTGGTCGGAGGCCTGAGCCACAGCTCCATCTCCCGCCTCAAGGAGACTCACAGTCATGTTAGCTCTGAGACC
```

Exon 8

```
      [G   F   R   F   P   I   L   G   V   H   L   K   D   L   V   A   L   Q   L   A   L   P   D]   W   L
D  GGTTTCCGCTTTCCTATCCTGGGTGTACACCTCAAGGACCTGGTGGCTCTGCAGCTGGCACTGCCTGACTGGCTG
B  GGTTTCCGCTTTCCTATCCTGGGTGTACACCTCAAGGACCTGGTGGCTCTGCAGCTGGCACTGCCTGACTGGCTG
S  GGGTTTCCGCTTTCCTATCCTGGGTGTACACCTCAAGGACCTGGTGGCTCTGCAGCTGGCACTGCCTGACTGGCT
L  GGTTTCCGCTTTCCTATCCTGGGTGTACACCTCAAGGACCTGGTGGCTCTGCAGCTGGCACTGCCTGACTGGCTG
M  GGTTTCCGCTTTCCTATCCTGGGTGTACACCTCAAGGACCTGGTGGCTCTGCAGCTGGCACTGCCTGACTGGCTG
C  GGTTTCCGCTTTCCTATCCTGGGTGTACACCTCAAGGACCTGGTGGCTCTGCAGCTGGCACTGCCTGACTGGCTG
```

```
        328(982)
      D   P   A   R   T   [R   L   N   G   A   K]   M   K   Q   L   F   S   I   L   E   E   L   A   M   V
D  GACCCTGCCCGGACCCGACTTAATGGGGCCAAGATGAAGCAGCTCTTCAGCATCCTGGAGGAGCTGGCCATGGTG
B  GACCCTGCCCGGACCCGACTTAATGGGGCCAAGATGAAGCAGCTCTTCAGCATCCTGGAGGAGCTGGCCATGGTG
S  GGACCCTGCCCGGACCCGACTTAATGGGGCCAAGATGAAGCAGCTCTTCAGCATCCTGGAGGAGCTGGCCATGGT
L  GACCCTGCCCGGACCTGACTTAATGGGGCCAAGATGAAGCAGCTCTTCAGCATCCTGGAGGAGCTGGCCATGGTG
M  GACCCTGCCCGGACCCGACTTAATGGGGCCAAGATGAAGCAGCTCTTCAGCATCCTGGAGGAGCTGGCCATGGTG
C  GACCCTGCCCGGACCCGACTTAATGGGGCCAAGATGAAGCAGCTCTTCAGCATCCTGGAGGAGCTGGCCATGGTG
```

Exon 9

```
      D   E   [L   Y   Q   L   S   L   Q   R   E   P   R]   S   K   S   S
D  GATGAACTCTACCAGCTGTCCCTGCAGCGGGAGCCACGCTCCAAGTCCTCG
B  GATGAACTCTACCAGCTGTCCCTGCAGCGGGAGCCACGCTCCAAGTCCTCG
S  GGATGAACTCTACCAGCTGTCCCTGCAGCGGGAGCCACGCTCCAAGTCCTC
L  GATGAACTCTACCAGCTGTCCCTGCAGCGGGAGCCACGCTCCAAGTCCTCG
M  GATGAACTCTACCAGCTGTCCCTGCAGCGGGAGCCACGCTCCAAGTCCTCG
C  GATGAACTCTACCAGCTGTCCCTGCAGCGGGAGCCACGCTCCAAGTCCTCG
```

Figure 5

PAR1

HUMAN   PR*SFLLRNPNDKYEPFWXXEDEEKN
CANINE  PR*SFFLKNTNDGFEPFPLEEDEEKN

H CCCCGG*TCATTTCTTCTCAGGAACCCCAATGATAAATATGAACCATTTTGGXXXXXXGAGGATGAGGAGAAAAAT
C CCCCGG*TCATTTTTTCTCAAGAATACCAATGATGGATTTGAACCATTCCCACTGGAGGATGATGAGGAGAAAAAT

*Cleavage site for human and dog (activation peptides are SFLLRN or SFFLKN, respectively)

PAR4

HUMAN   PR*GYPGQVCANDSDTLELPESSRAL
CANINE  LR*SFPGQPWANNSDILEIPESSRAL
MURINE  PR*GYPGKFCANDSDTLELPASSQAL

H CCCCGC*GGCTACCCAGGCCAAGTCTGTGCCAATGACAGTGACACCCTGGAGCTCCCGGACAGCTCACGGGCACTG
C CTGCGC*AGCTTCCCCGGCCAGCCCTGGGCTAACAACAGCGAGATCTTGGAGATCCCAGAAAGCTCCCGCGCCCTG
M CCACGA*GGCTACCCGGGCAAATTCTGTGCCAACGACAGTGACACGCTGGAGCTCCCGGCCAGCTCTCAAGCACTG

*Cleavage sites for human, dog, and mouse (activation peptides are GYPGQV, SFPGQP, or GYPGKF, respectively)

PAR3

HUMAN   IK*TFRGAPPNSFEEFPFSALEGWTX
CANINE  IK*TFRGAPSNSFEEFPLSAIEGWTE
MURINE  IK*SFNGAPQNTFEEFPLSDIEGWTX

H ATTAAG*ACCTTTCGTGGAGCTCCCCCAAATTCTTTTGAAGAGTTCCCCTTTTCTGCCTTGGAAGGCTGGACAXXX
C ATCAAG*ACCTTCCGTGGGGCTCCCTCAAATTCTTTTGAAGAGTTCCCCCTTTCTGCCATAGAAGGCTGGACAGAA
M ATTAAG*AGTTTTAATGGGGGTCCCCAAAATACCTTTGAAGAATTCCCACTTTCTGACATAGAGGGCTGGACAXXX
*Cleavage sites for human, dog, and mouse (activation peptides are TFRGAP, TFRGAP, or SFNGAP, respectively)

CAIDAG-GEF1 GENE MUTATIONS ASSOCIATED WITH THROMBOPATHY IN CANINES

CROSS-REFERENCE TO RELATED APPLICATIONS

The present application claims the benefit under 35 U.S.C. §119(e) to U.S. provisional application No. 60/853,401, filed on Oct. 19, 2006, and to U.S. provisional application No. 60/881,771, filed on Jan. 22, 2007, the contents of which are incorporated herein by reference in their entireties.

BACKGROUND

The present invention relates to methods and compositions for detecting mutations associated with thrombopathy. In particular, the invention relates to methods and composition for detecting mutations in the CalDAG-GEF1 gene that are associated with thrombopathy.

The platelet integrin alphaIIb-beta3, also known as the platelet glycoprotein complex IIb-IIIa, mediates platelet aggregation by binding the dimeric ligand fibrinogen. In unactivated platelets, the integrin is in a low-affinity/avidity state for the binding of fibrinogen. The conversion from a low-affinity to a high-affinity state is mediated by signal transduction proteins mobilized in response to agonists binding to specific receptors on the platelet surface; this sequence of events is termed "inside-out" signaling (R. O. Hynes, Cell 110:673-687 (2002); S. J. Shattil and P. J. Newman, Blood 104:1606-1615 (2004)). Examples of agonists that can induce "inside-out" signaling and thus change the affinity of the integrin for fibrinogen include ADP, collagen, thromboxane, and thrombin. Once fibrinogen has bound to alphaIIb-beta3, signal transduction events referred to as "outside-in" signaling occur, which increase the avidity of the integrin for fibrinogen and are accompanied by integrin receptor clustering.

Rap1 is a Ras-related low-molecular-weight guanine-nucleotide-binding protein (GTPase) that is ubiquitously expressed in high levels in platelets, neutrophils, and brain (J. L. Bos, EMBO J 17:6776-6782 (1998)). Rap1 seems to play an important role in several cell processes, including cell proliferation and differentiation, platelet, neutrophil, and B-cell activation, induction of T-cell anergy, and the regulation of the respiratory burst in neutrophils (J. L. Bos, All in the family? New insights and questions regarding interconnectivity of Ras, Rap1 and Ral, EMBO J 17:6776-6782 (1998)). Rap1 is activated by many different stimuli in different cell types and is thus a shared (common) component in signaling. Receptor-signaled generation of second messengers, including calcium, cAMP, and DAG can lead to the direct activation of Rap1-specific guanine nucleotide exchange factors (GEFs).

Platelets contain high levels of Rap1b. In platelets, Rap1 is involved in integrin activation and is activated by the binding of GTP and inactivated by the hydrolysis of bound GTP to GDP. In quiescent platelets, Rap1b is primarily localized to the plasma membrane (E. G. Lapetina et al, Proc Natl Acad Sci USA 86:3131-3134 (1989)). After activation, Rap1b relocalizes to the actin cytoskeleton (T. H. Fischer et al., J Biol Chem 265:19405-19408 (1990)). Platelet agonists that stimulate fibrinogen binding to platelet integrin alphaIIb-beta3 also stimulate binding of GTP to Rap1b resulting in its rapid activation (B. Franke et al., EMBO J 16:252-259 (1997); M. Torti and E. G. Lapetina, Proc Natl Acad Sci USA 89:7796-7800 (1992),). Most physiologic agonists (including ADP and collagen) that stimulate Rap1b activation do so through stimulation of Gi-coupled receptors (P. Lova et al., J Biol Chem 277:12009-12015 (2002); D. Woulfe et al., J Biol Chem 277:23382-23390 (2002)). Platelet adhesion mediated by binding of the platelet integrin alpha2-beta1 to collagen initiates outside-in signaling pathways that also result in activation of Rap1b (B. Bernardi et al, Blood 107:2728-2735 (2006)). Agonists that activate platelets through Gq-coupled receptors, including thromboxane, or through cross-linking of FcγRIIA, which is a tyrosine kinase-based pathway, rely on binding of secreted ADP, which in turn binds to the Gi-coupled ADP receptor P2Y12 (P. Lova et al., J Biol Chem 277: 12009-12015 (2002)). The importance of Rap1b for normal platelet function and hemostasis was demonstrated recently in a knockout mouse model. Rap1b null mice exhibited markedly impaired platelet function and experienced 85% embryonic and perinatal lethality primarily caused by hemorrhage-related events (M. Chrzanowska-Wodnicka et al, J Clin Invest 115:680-687 (2005)).

Calcium-Diacylglycerol Guanine Nucleotide Exchange Factor I (CalDAG-GEFI) is a GEF that activates Rap1b. CalDAG-GEFI contains 4 major domain structures: (1) a Ras exchanger motif (REM) domain common to Ras family GEFs; (2) a cdc25-like GEF domain (catalytic domain); (3) two EF hand domains for interaction with calcium; and (4) a C1 domain for interaction with DAG and phorbol esters. Guanine nucleotide exchange factors promote nucleotide release from GTPases. GDP is not preferentially released over GTP; cellular concentrations of GTP are generally 10 times higher than concentrations of GDP; thus, GTP has a higher likelihood of rebinding to the GTPase than GDP (P. A. Boriack-Sjodin et al., Nature 394: 337-343 (1998)). The exchange of GTP for GDP promotes the activity of GTPases. CalDAG-GEFI knockout mice exhibit severely impaired platelet aggregation and release responses to most agonists, including ADP, collagen, thromboxane, and the calcium ionophore A23187 (J. R. Crittenden et al., Nat Med 10:982-986 (2004)). CalDAG-GEFI effects are likely caused by affinity/avidity modulation of integrin alphaIIb-beta3 via activation of Rap1b (A. Bertoni et al, J Biol Chem 277 (2002), pp. 25715-25721). It is possible, however, not all the CalDAG-GEFI effects on platelet function reported in the knockout mice may be linked to activation of Rap1b.

Intrinsic platelet function disorders have been described in Basset hounds and Eskimo Spitz dogs (I. B. Johnstone and F. Lotz, Can Vet J 20:211-215 (1979); J. L. Catalfamo et al., Blood 67:1568-1577 (1986); M. K. Boudreaux et al., J Vet Int Med 8:93-98 (1994)). A platelet defect has been recognized in Landseers, a European dog breed related to the Newfoundland breed; however, biochemical and functional descriptions of the disorder are lacking. Affected Basset hounds, Spitz dogs, and Landseers experience epistaxis, gingival bleeding, and petechiation on mucous membranes and skin. Platelet number, plasma von Willebrand factor concentration, and function and coagulation screening assays are normal, whereas bleeding time tests are prolonged. In contrast to Rap1b null mice, reduced litter sizes or high neonatal lethality have not been described with these disorders in dogs.

The platelet disorders in Basset hounds and Spitz dogs have been well characterized, and they are essentially similar at the functional level. Platelet aggregation responses to ADP, collagen, calcium ionophore A23187, and platelet activating factor (PAF) are severely impaired. In response to thrombin, their platelets exhibit a characteristic lag phase with normal maximal extent aggregation. Epinephrine enhances the sensitivity of thrombopathic platelets to ADP, but the aggregation response is still reduced compared with normal platelets.

Thrombopathic Basset hound intraplatelet fibrinogen content and concentrations of membrane glycoproteins IIb and IIIa are normal. Platelets from affected Basset hounds and Spitz dogs support normal clot retraction. cDNA sequences and coding areas of genomic DNA for platelet glycoproteins IIb and IIIa obtained from affected Basset hounds and heterozygous Landseers are identical to sequences obtained for normal dogs except for the presence of benign polymorphisms (Boudreaux, unpublished findings). The similarity of the platelet function disorder described in affected dogs to that identified in CalDAG-GEFI knockout mice, combined with the lack of embryonic or neonatal lethality described in the CalDAG-GEFI mouse knockout, prompted the evaluation of the gene encoding CalDAG-GEFI in affected Basset hounds, in an affected Eskimo Spitz dog, and in an affected Landseer. Three distinct CalDAG-GEFI gene mutations were identified in each breed evaluated.

Intrinsic platelet disorders also have been described in Simmental cattle (Steficek et al., J Vet Diagn Invest 5:202-7 (1993); Searcy et al., Can J. Vet. Res. 54:394-396 (1990). A distinct CalDAG-GEF1 gene mutation likewise was identified in Simmental cattle.

All mutations were located in portions of the gene encoding the highly conserved catalytic unit. The changes are considered significant and would result in either lack of synthesis, enhanced degradation, or marked impairment of protein function.

SUMMARY

Disclosed are methods and compositions for detecting mutations and diagnosing diseases or disorders associated with thrombopathy. In particular, the invention relates to methods and composition for detecting mutations in the CalDAG-GEF1 gene that are associated with thrombopathy.

The disclosed methods include methods for diagnosing a subject as a carrier of a mutant gene associated with thrombopathy. The methods may include analyzing all or part of a nucleic acid sequence in a biological sample from the subject to determine whether a mutation in the CalDAG-GEF1 gene is present, where, if the mutation is present, the subject is diagnosed as a carrier of a mutant gene associated with thrombopathy. The methods typically include detecting at least one mutation in CalDAG-GEF1 gene that is associated with thrombopathy. In some embodiments, the methods may include methods for predicting the likelihood that a subject will develop thrombopathy, where the presence of at least one mutation in the CalDAG-GEF1 gene is indicative of an increased risk of thrombopathy. Optionally, the mutation is present in the catalytic domain of CalDAG-GEF1 (e.g., within one of the five (5) structurally conserved regions (SCR1-5), as discussed herein).

Subjects for the disclosed methods may include human or non-human animals. In some embodiments, subjects may include canines (e.g., Basset hounds, Spitz such as Eskimo Spitz, and Landseers) and bovines (e.g., Simmental cattle).

The methods disclosed herein may be used to diagnose hereditary thrombopathy which is associated with platelet aggregation disorders and impaired platelet release responses. The thrombopathy may be characterized by epistaxis, gingival bleeding, or petechiation (e.g., in a subject that is homozygous for a mutant CalDAG-GEF1 gene associated with the thrombopathy).

The methods typically include detecting at least one mutation in a CalDAG-GEF1 gene of a subject. A mutant CalDAG-GEF1 gene that includes the mutation may encode a CalDAG-GEF1 polypeptide that is defective in comparison to wild-type CalDAG-GEF1 polypeptide. The mutant CalDAG-GEF1 may exhibit a biological or functional activity that is reduced in comparison to wild-type CalDAG-GEF1 polypeptide. The mutation may be a loss of function mutation (or reduction in function mutation) with respect to Rap1-specific guanine nucleotide exchange factor activity.

The detected mutation may include one or more of the following: an insertion of one or more nucleotides (which optionally may result in a frameshift in the coding sequence); a deletion of one or more nucleotides (which optionally may result in a frameshift in the coding sequence and/or delete one or more conserved amino acids as discussed herein); and a substitution of one or more nucleotides (which optionally results in a mutation that is not silent with respect to the coding sequence and optionally may result in a non-conservative amino acid substitution as discussed herein).

The disclosed methods may include analyzing a sample that comprises nucleic acid, which may include genomic DNA, cDNA, and/or mRNA. The methods may include performing nucleic amplification (e.g., PCR) and/or sequencing. The methods may include performing reverse transcription (e.g., to create cDNA from mRNA). The methods may include performing a comparison of the nucleic acid sequence of a subject's nucleic acid to the nucleic acid sequence of a wild-type sequence.

In some embodiments, the methods include performing hybridization using at least one oligonucleotide that hybridizes to a CalDAG-GEF1 gene. The oligonucleotide may specifically hybridize to a CalDAG-GEF1 gene that optionally includes at least one mutation, and optionally, the oligonucleotide may not specifically hybridize to a wild-type CalDAG-GEF1 gene. The oligonucleotide may be suitable for detecting at least one mutation in the CalDAG-GEF1 gene. In some embodiments, oligonucleotides suitable for detecting mutations in a CalDAG-GEF1 gene may include oligonucleotides comprising a nucleotide sequence selected from the group consisting of SEQ ID NOs:8-15, 24, and 25.

In some embodiments, the methods may include detecting at least one mutation in a canine. The detected mutation may be selected from the group consisting of: an insertion of A between nucleotides 452 and 453 of SEQ ID NO:2; a deletion from nucleotide 509 to nucleotide 511 of SEQ ID NO:2; and a substitution of T for C at nucleotide position 982 of SEQ ID NO:2. In particular, the canine may be a Basset hound and the mutation may be a deletion from nucleotide 509 to nucleotide 511 of SEQ ID NO:2, resulting in a deletion of a phenylalanine residue at amino acid position 170 of SEQ ID NO:3. The canine may be a Spitz (e.g., an Eskimo Spitz) and the mutation may be an insertion of an adenine between nucleotide 452 and 453 of SEQ ID NO:2, producing a frameshift in the coding sequence and resulting in an encoded polypeptide that has the amino acid sequence of SEQ ID NO:7 at its C-terminus. The canine may be a Landseer and the mutation may be a substitution of a thymine for cytosine at nucleotide position 982 of SEQ ID NO:2, producing a premature stop codon in the coding sequence and resulting in a truncated CalDAG-GEF-1 polypeptide. The methods may include specifically detecting a polynucleotide comprising a nucleotide sequence of any of SEQ ID NOs:3-5.

In further embodiments, the methods may include detecting at least one mutation in a bovine. The detected mutation may include a substitution of C for T at nucleotide position 701 of SEQ ID NO:16. The bovine may be Simmental cattle. The methods may include specifically detecting a polynucleotide comprising a nucleotide sequence of any of SEQ ID NOs:17-19.

Kits for performing the methods also are contemplated. In some embodiments, the kits include at least oligonucleotide that specifically hybridizes to a canine or bovine CalDAG-GEF1 polynucleotide. The kit may include at least one oligonucleotide suitable for detecting a mutation in a CalDAG-GEF1 polynucleotide. For example, the kit may include an oligonucleotide comprising a nucleotide sequence selected from the group consisting of SEQ ID NOs:8-15, 24 and 25. The oligonucleotide may include a label (e.g., a fluorophore or a radiolabel).

The disclosed methods may include methods for diagnosing a subject as a carrier for a mutant CalDAG-GEF1 gene associated with thrombopathy, where the method includes detecting a mutant CalDAG-GEF1 polypeptide encoded by the mutant CalDAG-GEF1 gene. In some embodiments, the methods may include reacting a biological sample from the subject with a reagent that detects a polypeptide encoded by the mutant CalDAG-GEF1 gene. For example, an encoded mutant polypeptide may be distinguished from wild-type polypeptide by the reagent, based on the mutant polypeptide having a different amino acid sequence (e.g., due to a frameshift) or a different molecular weight (e.g., where the mutant CalDAG-GEF1 polypeptide is truncated in comparison to the wild-type polypeptide, as for the polypeptide encoded by SEQ ID NO:6 in comparison to the polypeptide encoded by SEQ ID NO:2). The reagent may include an antibody or a binding fragment thereof that binds specifically to the polypeptide to form a complex and immunoassays also are contemplated. The reagent may be labeled for detection (e.g., with a fluorophore or a radiolabel).

Isolated polynucleotides, polypeptides, variants, mutants, or fragments thereof also are contemplated herein, for example, isolated polynucleotides comprising a nucleotide sequence of any of SEQ ID NOs:1-5, 8-19, 24, 25, 31-35, 41 and 42 and isolated polypeptides comprising an amino acid sequence of any of SEQ ID NOs:6, 7, 20-23, 26-30, and 36-38. Isolated polynucleotides encoding polypeptides comprising an amino acid sequence of any of SEQ ID NOs:6, 7, 20-23, 26-30, and 36-38 also are contemplated. Variants, mutants, and/or fragments of the isolated polynucleotides and polypeptides also are contemplated. In some embodiments, variants, mutants, and/or fragments of the isolated polynucleotides or polypeptides may have at least about 95%, 96%, 97%, 98%, or 99% sequence identity to a reference polynucleotide or polypeptide. Fragments may comprise at least about 6, 8, 10, 12, 14, 16, 18, 20, 100, or 200 contiguous nucleotides or amino acids of a full length reference polynucleotide or polypeptide. Antibodies or antibody binding fragments that specifically bind to the isolated polypeptides, variants, mutants, or fragments thereof also are contemplated (e.g., antibodies or antibody binding fragments that bind to a polypeptide encoded by polynucleotides of any of SEQ ID NOs:1-5, 8-19, 24, 25, 31-35, 41 and 42 or a polypeptide comprising an amino acid sequence of any of SEQ ID NOs:6, 7, 20-23, 26-30, and 36-38).

BRIEF DESCRIPTION OF THE FIGURES

FIG. 1 shows the primer sets used to amplify cDNA and DNA segments of the gene encoding CalDAG-GEFI. The length of the segments amplified are indicated following the primer sets (bp=base pairs).

FIG. 3 displays a partial DNA sequence of the gene encoding CalDAG-GEFI in dogs. Amino acid letter designations are shown for normal canine sequence above each codon. Numbering of amino acids and nucleotides begins with ATG. Nucleotide numbers are in parentheses following the amino acid number for selected codons. D=Boxer, dog genome; B=thrombopathic Basset hound; S=thrombopathic Eskimo Spitz; L=thrombopathic Landseer; M=mixed-breed dog, non-bleeder; C=Cavalier King Charles Spaniel with macrothrombocytopenia and enhanced platelet reactivity. Bracketed section [FDHLEPLELAEHLTYLEYRSFCKI]=SCR1 in Exon 5 (SEQ ID NO:26). Eskimo Spitz dogs with thrombopathia have a single nucleotide insertion (A) between nucleic acids 452 and 453 (452-453insA) resulting in a frame shift. Basset hounds with thrombopathia have a 3 nucleotide deletion (XXX=TCT) at nucleotide positions 509, 510, 511 (509, 510, 511delTCT), which would result in the deletion of a phenylalanine at amino acid position 170. Bracketed section [RALVITHFVHVAEKLLHLQNFNTLMAV-VGGLSHSSISRLKETH]=SCR2 in Exons 6 and 7 (SEQ ID NO:27). Eskimo Spitz dogs with thrombopathia have a premature stop codon appearing at nucleotide position 796 because of a frame shift starting at nucleotide position 453 (S266Stop). Bracketed section [GFRF-PILGVHLKDLVALQLALPD]=SCR3 in Exon 8 (SEQ ID NO:28). Bracketed section [RLNGAK]=SCR4 in Exon 8 (SEQ ID NO:29). Landseers with thrombopathia have a single nucleotide substitution at nucleotide position 982 (982C>T) resulting in the appearance of a premature stop codon (R328Stop) within SCR4). Bracketed section [LYQLSLQREPR]=SCR5 in Exon 9 (SEQ ID NO:30).

FIG. 5 displays partial cDNA sequences encoding PAR1 (i.e., "Protease Activated Receptor 1"), PAR4, and PAR3 in dog (C) compared to human (H) and mouse (M) sequences obtained from GenBank. Encoded amino acids (letter designations) are shown. cDNA sequences encompass regions encoding the cleavage sites for the activation peptides. Cleavage sites determined for mouse and human and proposed cleavage sites for dog are indicated (*). Activation peptides are underlined. X's are used to designate absence of nucleotides or amino acids observed during sequence alignment.

DETAILED DESCRIPTION

Figure 2:
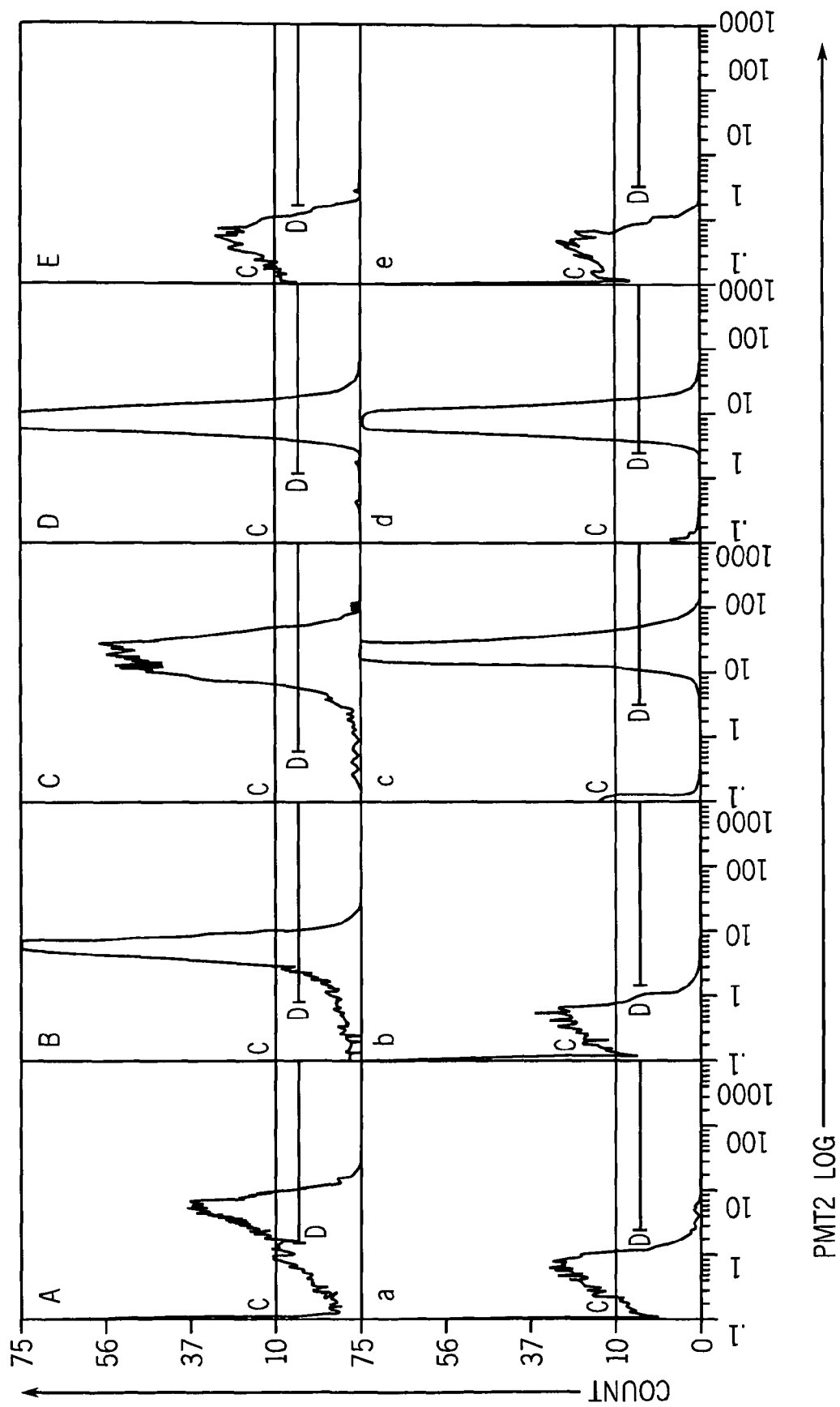
FIG. 2 shows representative flow cytometric results obtained from a normal dog (upper panel, A through E) and a thrombopathic Basset hound (lower panel, a through e). Aa. Mouse anti-RIBS on canine fibrinogen (CAP1) in response to 100 µM ADP, ("RIBS"=receptor induced binding site). Bb. Mouse anti-RIBS on canine fibrinogen (CAP1) in response to 0.2 µM PAF, ("PAF"=Platelet Activating Factor). Cc. Mouse anti-human GPIIb (alpha IIb). Dd. Mouse anti-human GPIIIa (beta 3) ("GPIIIa"=GlycoProtein IIIa). Ee. Isotype control. Platelets from Basset hounds with thrombopathia did not bind CAP1, a monoclonal antibody to a RIBS on canine fibrinogen in response to ADP or PAF (A and B). Similar findings were found using a wide range of ADP and PAF concentrations. Thrombopathic platelets bound antibodies to GPIIb and GPIIIa in a manner similar to normal canine platelets (C and D). Similar results were found for platelets from a Spitz dog with thrombopathia.

To facilitate an understanding of the present invention, a number of terms and phrases are defined below.

Unless otherwise noted, the terms used herein are to be understood according to conventional usage by those of ordinary skill in the relevant art. In addition to the definitions of terms provided below, it is to be understood that as used in the specification, embodiments, and claims, "a" or "an" can mean one or more, depending upon the context in which it is used.

As used herein, "about", "approximately," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "significantly" will mean more than plus or minus 10% of the particular term.

As used herein, the term "subject" refers to any animal (e.g., a mammal), including, but not limited to, canines, bovines, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals. Such non-human animals include, but are not limited to, vertebrates such as canines, bovines, rodents, non-human primates, ovines, bovines, lagomorphs, porcines, caprines, equines, felines, and aves.

As used herein, the term "subject suspected of having thrombopathy" refers to a subject that presents one or more symptoms indicative of thrombopathy (e.g., epistaxis, gingival bleeding, and petechiation). Thrombopathy may be associated with platelet aggregation disorders and impaired platelet release responses in the presence of agonists (e.g., ADP, collagen, thromboxane, and calcium ionophores such as A23187). A subject diagnosed with thrombopathy may exhibit an absent, impaired, elevated or atypical response in one or more tests listed in Table 1. Typically, the thrombopathy discussed herein is hereditary thrombopathy. A subject suspected of carrying a mutant gene associated with thrombopathy may include a subject that is heterozygous for the mutant gene or homozygous for the mutant gene. The mutant gene may be recessive or dominant. Thrombopathy may include thrombopathy of animals (e.g., Basset Hound Hereditary Thrombopathy). As used herein, the term "diagnosing" includes providing information regarding the presence of a gene associated with thrombopathy in a subject (e.g., as determined by the diagnostic methods of the present invention).

As used herein, the term "instructions for using a kit for detecting a mutation" includes instructions for using the reagents contained in the kit for the detection and characterization of the mutation in a sample from a subject. In some embodiments, the instructions further comprise the statement of intended use required by the U.S. Food and Drug Administration (FDA) in labeling in vitro diagnostic products.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence (as a fragment) and optionally, the portion or fragment may retain a desired activity or functional properties (e.g., enzymatic activity, ligand binding, signal transduction, immunogenicity, etc.) of the full-length polypeptide. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As discussed herein, a mutant gene includes at least one mutation relative to the wild-type gene. Mutations may include insertions, deletions, and/or substitutions (e.g., non-silent substitutions with respect to an encoded polypeptide). Mutations may result in a mutant polypeptide that is functionally impaired with respect to the wild-type polypeptide. A mutant CalDAG-GEF1 polypeptide may exhibit impaired Rap1-specific guanine nucleotide exchange factor activity relative to a wild-type CalDAG-GEF1 polypeptide. Other impaired functional activities may include reduced binding to calcium and reduced binding to diacylglycerol and phorbol esters. The specific activity of a mutant CalDAG-GEF1 polypeptide may be reduced at least about 50%, 60%, 70%, 80%, 90%, 95%, or 99% relative to a wild-type CalDAG-GEF1 polypeptide. The functional activity of a mutant or wild-type CalDAG-GEF1 polypeptide may be measured using methods described herein or known in the art. (See Kawasaki et al., PNAS 95:13278-13283 (1998); Dupuy et al., J. Biol. Chem. 276:11804-11811 (2001); Eto et al, PNAS 99:12819-12824 (2002); and Boudreax et al., Translation Res. 150:81-92 (2007), the contents of which are incorporated herein by reference in their entireties).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotide or polynucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element or the coding region. Transcription termination and polyadenylation signals are located 3' or downstream of the coding region.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target. The "percent identity" between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using mathematical algorithms. "Percentage sequence identity" may be determined by aligning two sequences using the Basic Local Alignment Search Tool available at the NBCI website (i.e., "bl2seq" as described in Tatiana A. Tatusova, Thomas L. Madden (1999), "Blast 2 sequences—a new tool for comparing protein and nucleotide sequences", FEMS Microbiol Lett. 174:247-250)).

Variant polynucleotides are contemplated herein and may include polynucleotides having at least about 95% sequence identity (or at least about 96%, 97%, 98%, or 99% sequence identity) to a reference polynucleotide (e.g., a wild-type polynucleotide where the variant polynucleotide is a mutant). Variant polypeptides also are contemplated herein and may include polypeptides having at least about 95% sequence identity (or at least about 96%, 97%, 98%, or 99% sequence identity) to a reference polypeptide (e.g., a wild-type polypeptide where the variant polypeptide is a mutant). Variants may include fragments of a full-length reference polynucleotide or polypeptide as disclosed herein. Variant polypeptides may have a substantially similar functional or biological activity as a wild-type polypeptide or may have a diminished functional or biological activity in comparison to a wild-type polypeptide. For example, a variant polypeptide may exhibit an functional or biological activity that is reduced at least about 50%, 60%, 70%, 80%, 90%, 95%, or 99% in comparison to wild-type polypeptide.

Mutants or variants include at least one mutation relative to a wild-type polynucleotide or polypeptide. Mutations may include deletions or insertions of one or more nucleotides (which optionally may produce a frameshift in the coding sequence of a polynucleotide). A mutant polypeptide may include an amino acid sequence that is truncated with respect to a wild-type polypeptide (e.g., truncated at least about 10%, 20%, 30%, 40%, or 50% with respect to a wild-type polypeptide). A mutant polypeptide may include a frameshift which produces an amino acid sequence at the C-terminus of the mutant polypeptide that is different than the wild-type polypeptide. Mutations also may include one or more nucleotide substitutions, which optionally may be non-silent with respect to the coding sequence of a polynucleotide and may create a premature stop codon in the reading frame. Nucleotide substitutions may result in amino acid substitutions for an encoded polypeptide. Amino acid substitutions may include "conservative" or "non-conservative" amino acid substitutions as understood in the art. For example, the substitution of a non-polar amino acid (e.g., leucine, alanine, or isoleucine) for a polar amino acid (e.g., lysine, asparagine, glutamic acid, or aspartic acid) is a "non-conservative" amino acid substitution.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization (1985)). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$.H$_2$O and 1.85 g/l EDTA, pH adjusted to 7.4 with NaOH), 0.1% SDS, 5× Denhardt's reagent (50× Denhardt's contains per 500 ml: 5 g Ficoll (Type 400, Pharamcia), 5 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (see definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are thought to be sorted out from other nucleic acid. Amplification techniques have been designed primarily for this sorting out.

Template specificity is achieved in most amplification techniques by the choice of enzyme. Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989)).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target". In contrast, "background template" is used in reference to nucleic acid other than sample template that may or may not be present in a sample. Background template is most often inadvertent. It may be the result of carryover, or it may be due to the presence of nucleic acid contaminants thought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest.

A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications. As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are mixed to form an amplification mixture which may be placed and contained in a reaction vessel (test tube, microwell, etc.).

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "sample" is used in its broadest sense. In one sense, it is meant to include a specimen or culture obtained from any source (e.g., a biological sample from a subject or patient). Biological samples may be obtained from animals (including humans) and encompass fluids, solids, and tissues. Biological samples include blood products, such as platelets, plasma, serum and the like. Such examples are not however to be construed as limiting the sample types applicable to the present invention.

ILLUSTRATIVE EMBODIMENTS

The following embodiments are provided in order to demonstrate and further illustrate certain preferred aspects of the present invention and are not to be construed as limiting the scope thereof.

Embodiment 1

A method for diagnosing a canine as a carrier of a mutant gene associated with thrombopathy, the method comprising analyzing all or part of a nucleic acid sequence in a biological sample from the canine to determine whether at least one mutation in the CalDAG-GEF1 gene is present, wherein the presence of at least one mutation indicates that the canine is a carrier of the mutant gene associated with thrombopathy.

Embodiment 2

A method for detecting a mutation associated with thrombopathy in a canine, the method comprising analyzing all or part of a nucleic acid sequence corresponding to a CalDAG-GEF1 gene in a biological sample from the canine to determine whether at least one mutation in the CalDAG-GEF1 gene is present, wherein the mutation is associated with thrombopathy.

Embodiment 3

A method for predicting the likelihood that a canine will develop thrombopathy, the method comprising analyzing all or part of a nucleic acid sequence corresponding to a CalDAG-GEF1 gene in a biological sample from the canine to determine whether at least one mutation in the CalDAG-GEF1 gene is present, wherein the presence of the at least one mutation is indicative of an increased risk of thrombopathy.

Embodiment 4

The method of any of embodiments 1-3, wherein the thrombopathy comprises a platelet aggregation disorder.

Embodiment 5

The method of embodiment 4, wherein the platelet aggregation disorder is characterized by epistaxis, gingival bleeding, or petechiation.

Embodiment 6

The method of any of embodiments 1-5, wherein the mutation is selected from the group consisting of: an insertion of A between nucleotides 452 and 453 of SEQ ID NO:2; a deletion from nucleotide 509 to nucleotide 511 of SEQ ID NO:2; and a substitution of T for C at nucleotide position 982 of SEQ ID NO:2.

Embodiment 7

The method of any of embodiments 1-6, wherein the canine belongs to a breed selected from the group consisting of Basset hound, Spitz, and Landseer breeds.

Embodiment 8

The method of any of embodiments 1-7, wherein the canine is a Basset hound and the mutation is a deletion from nucleotide 509 to nucleotide 511 of SEQ ID NO:2.

Embodiment 9

The method of any of embodiments 1-7, wherein the canine is a Spitz and the mutation is an insertion of A between nucleotides 452 and 453 of SEQ ID NO:2.

Embodiment 10

The method of any of embodiments 1-7, wherein the canine is a Landseer and the mutation is a substitution of T for C at nucleotide position 982 of SEQ ID NO:2.

Embodiment 11

The method of any of embodiments 1-10, wherein the mutation is a loss of function mutation with respect to Rap1-specific guanine nucleotide exchange factor activity.

Embodiment 12

The method of any of embodiments 1-11, wherein the mutation is an insertion or a deletion that results in a frame shift.

Embodiment 13

The method of any of embodiments 1-12, wherein the mutation is a nucleotide substitution that results in a stop codon.

Embodiment 14

The method of any of embodiments 1-13, wherein the nucleic acid sequence analyzed is genomic DNA, cDNA, or mRNA.

Embodiment 15

The method of any of embodiments 1-14, wherein analyzing comprises performing hybridization using at least one oligonucleotide that specifically hybridizes to a CalDAG-GEF1 gene comprising the mutation.

Embodiment 16

The method of embodiment 15, wherein the oligonucleotide does not hybridize to a wild-type CalDAG-GEF1 gene.

Embodiment 17

The method of embodiment 15 or 16, wherein the oligonucleotide comprises a nucleotide sequence selected from the group consisting of SEQ ID NOs:8-15.

Embodiment 18

The method of any of embodiments 1-17, wherein analyzing comprises performing nucleic acid amplification.

Embodiment 19

The method of any of embodiments 1-18, wherein analyzing comprises sequencing.

Embodiment 20

The method of any of embodiments 1-19, wherein the presence of the mutation is detected by comparing the nucleic acid sequence with wild-type sequence.

Embodiment 21

A kit for performing any of the methods of embodiments 1-20.

Embodiment 22

The kit of embodiment 21, comprising at least one oligonucleotide that specifically hybridizes to a canine CalDAG-GEF1 gene.

Embodiment 23

The kit of embodiment 21 or 22, wherein the oligonucleotide comprises a nucleotide sequence selected from the group consisting of SEQ ID NOs:8-15.

Embodiment 24

An isolated polynucleotide comprising a nucleotide sequence selected from the group consisting of SEQ ID NOs: 1-5, 8-15, 31, and 33-35, or a variant, mutant or fragment thereof.

Embodiment 25

A method for diagnosing a canine as a carrier for a mutant CalDAG-GEF1 gene associated with thrombopathy, the method comprising reacting a biological sample from the canine with a reagent that detects a polypeptide encoded by the mutant CalDAG-GEF1 gene.

Embodiment 26

A method for detecting a mutant CalDAG-GEF1 gene associated with thrombopathy in a canine, the method comprising reacting a biological sample from the canine with a reagent that detects a polypeptide encoded by the mutant CalDAG-GEF1 gene.

Embodiment 27

A method for predicting the likelihood that a canine will develop thrombopathy, the method comprising reacting a biological sample from the canine with a reagent that detects a polypeptide encoded by the mutant CalDAG-GEF1 gene.

Embodiment 28

The method of any of embodiments 25-27, wherein the reagent comprises an antibody or a binding fragment thereof that binds specifically to the polypeptide to form a complex.

Embodiment 29

The method of any of embodiments 25-27, wherein the mutant CalDAG-GEF1 gene comprises a mutation selected from the group selected from the group consisting of: an insertion of A between nucleotides 452 and 453 of SEQ ID NO:2; a deletion from nucleotide 509 to nucleotide 511 of SEQ ID NO:2; and a substitution of T for C at nucleotide position 982 of SEQ ID NO:2.

Embodiment 30

The method of any of embodiments 25-27, wherein the polypeptide comprises an amino acid sequence of SEQ ID NO:7.

Embodiment 31

An antibody that specifically binds to a mutant polypeptide encoded by any of SEQ ID NOs:3-5.

Embodiment 32

A mutant polypeptide encoded by any of SEQ ID NOs:3-5 or a variant or fragment thereof (for example a polypeptide comprising an amino acid sequence of SEQ ID NO:7 or a variant or fragment thereof).

Embodiment 33

A method for diagnosing a bovine as a carrier of a mutant gene associated with thrombopathy, the method comprising analyzing all or part of a nucleic acid sequence in a biological sample from the bovine to determine whether at least one mutation in the CalDAG-GEF1 gene is present, wherein the presence of the at least one mutation indicates that the bovine is a carrier of the mutant gene associated with thrombopathy.

Embodiment 34

A method for detecting a mutation associated with thrombopathy in a bovine, the method comprising analyzing all or part of a nucleic acid sequence corresponding to a CalDAG-GEF1 gene in a biological sample from the bovine to determine whether at least one mutation in the CalDAG-GEF1 gene is present, wherein the mutation is associated with thrombopathy.

Embodiment 35

A method for predicting the likelihood that a bovine will develop thrombopathy, the method comprising analyzing all or part of a nucleic acid sequence corresponding to a CalDAG-GEF1 gene in a biological sample from the bovine to determine whether at least one mutation in the CalDAG-GEF1 gene is present, wherein the presence of the at least one mutation is indicative of an increased risk of thrombopathy.

Embodiment 36

The method of any of embodiments 33-35, wherein the thrombopathy comprises a platelet aggregation disorder.

Embodiment 37

The method of embodiment 36, wherein the platelet aggregation disorder is characterized by epistaxis, gingival bleeding, or petechiation.

Embodiment 38

The method of any of embodiments 33-37, wherein the mutation is a substitution of C for T at nucleotide position 701 of SEQ ID NO:16.

Embodiment 39

The method of any of embodiments 33-38, wherein the bovine is a Simmental cattle.

Embodiment 40

The method of any of embodiments 33-39, wherein the mutation is a loss of function mutation with respect to Rap1-specific guanine nucleotide exchange factor activity.

Embodiment 41

The method of any of embodiments 33-40, wherein the nucleic acid sequence analyzed is genomic DNA, cDNA, or mRNA.

Embodiment 42

The method of any of embodiments 33-41, wherein analyzing comprises performing hybridization using at least one oligonucleotide that specifically hybridizes to a CalDAG-GEF1 gene comprising the mutation.

Embodiment 43

The method of embodiment 42, wherein the oligonucleotide does not hybridize to a wild-type CalDAG-GEF1 gene.

Embodiment 44

The method of embodiment 42 or 43, wherein the oligonucleotide comprises a nucleotide sequence selected from the group consisting of SEQ ID NOs:24 and 25.

Embodiment 45

The method of any of embodiments 33-44, wherein analyzing comprises performing nucleic acid amplification.

Embodiment 46

The method of any of embodiments 33-45, wherein analyzing comprises sequencing.

Embodiment 47

The method of any of embodiments 33-46, wherein the presence of the mutation is detected by comparing the nucleic acid sequence with wild-type sequence.

Embodiment 48

A kit for performing any of the methods of embodiments 33-47.

Embodiment 49

The kit of embodiment 48, comprising at least one oligonucleotide that specifically hybridizes to a bovine CalDAG-GEF1 gene.

Embodiment 50

The kit of embodiment 48 or 49, wherein the oligonucleotide comprises a nucleotide sequence selected from the group consisting of SEQ ID NOs:24 and 25.

Embodiment 51

An isolated polynucleotide comprising a nucleotide sequence selected from the group consisting of SEQ ID NOs: 16-19, 24, 25, 41, 42 or a variant, mutant, or fragment thereof.

Embodiment 52

A method for diagnosing a bovine as a carrier for a mutant CalDAG-GEF1 gene associated with thrombopathy, the method comprising reacting a biological sample from the bovine with a reagent that detects a polypeptide encoded by the mutant CalDAG-GEF1 gene.

Embodiment 53

A method for detecting a mutant CalDAG-GEF1 gene associated with thrombopathy in a bovine, the method comprising reacting a biological sample from the bovine with a reagent that detects a polypeptide encoded by the mutant CalDAG-GEF1 gene.

Embodiment 54

A method for predicting the likelihood that a bovine will develop thrombopathy, the method comprising reacting a biological sample from the bovine with a reagent that detects a polypeptide encoded by the mutant CalDAG-GEF1 gene.

Embodiment 55

The method of any of embodiments 52-54, wherein the reagent comprises an antibody or a binding fragment thereof that binds specifically to the polypeptide to form a complex.

Embodiment 56

The method of any of embodiments 52-54, wherein the mutant CalDAG-GEF1 gene comprises a substitution of C for T at nucleotide position 701 of SEQ ID NO:16.

Embodiment 57

An antibody that specifically binds to a mutant polypeptide encoded by a polynucleotide comprising a nucleotide sequence of any of SEQ ID NOs:16-19.

Embodiment 58

A mutant polypeptide encoded by a polynucleotide comprising a nucleotide sequence of any of SEQ ID NOs:16-19, or a variant or a fragment thereof (for example, a polypeptide comprising an amino acid sequence of SEQ ID NOs:20-23 or a variant or fragment thereof).

Embodiment 59

A method of detecting a mutation in a polynucleotide comprising a nucleotide sequence of any of SEQ ID NOs:1-5, 8-19, 24, 25, 31-35, 41 and 42, wherein the mutation is associated with thrombopathy.

Embodiment 60

A method of identifying a carrier of a gene associated with thrombopathy comprising detecting a mutation in a CalDAG-GEF1 nucleic acid (preferably detecting a mutation in any of SEQ ID NOs:1-5, 8-19, 24, 25, 31-35, 41 and 42).

Embodiment 61

The method of embodiment 60, wherein detecting comprises detecting a mutation in genomic DNA, a cDNA, or mRNA.

Embodiment 62

The method of embodiment 61, wherein detecting comprises detecting a mutant polypeptide encoded by a polynucleotide comprising a nucleotide sequence of any of SEQ ID NOs:1-5, 8-19, 24, 25, 31-35, 41 and 42.

Embodiment 63

An isolated polynucleotide comprising a nucleotide sequence of any of SEQ ID NOs:1-5, 8-19, 24, 25, 31-35, 41 and 42, or a variant or fragment thereof.

Embodiment 64

An isolated polypeptide encoded by a nucleotide sequence of any of SEQ ID NOs: 1-5, 8-19, 24, 25, 31-35, 41 and 42 or a polypeptide comprising an amino acid sequence of any of SEQ ID NOs:6, 7, 20-23, 26-30, and 36-38, or a variant, mutant or fragment thereof.

EXAMPLES

The following Examples (I-III) are provided in order to demonstrate and further illustrate certain preferred embodiments and aspects of the present invention and are not to be construed as limiting the scope thereof.

Example I

Gene Mutations in Basset Hounds, Eskimo Spitz, and Landseer Dogs with Intrinsic Platelet Function Disorders A. Introduction Basset hound thrombopathia (BHT) was first described by Johnstone and Lotz in 1979. Affected Basset hounds experienced epistaxis, gingival bleeding, and petechiation on mucous membranes and skin. Platelet counts, von Willebrand factor analyses, and coagulation screening assays were normal while bleeding time tests were prolonged, which focused the cause of bleeding at the level of platelet function. Platelet aggregation responses to collagen and ADP and calcium ionophore A23187 were markedly impaired. Platelets did aggregate in response to thrombin; however, the rate was impaired and there was a characteristic lag phase (Catalfamo et al 1986). Epinephrine enhanced the sensitivity of thrombopathic platelets to ADP but the aggregation response was still reduced compared to normal platelets. Dense granule secretion as demonstrated using $^{14}$C-serotonin was markedly impaired in thrombopathic platelets. Although uptake of serotonin was normal, thrombopathic platelets released less than 6% of their total platelet $^{14}$C-serotonin in response to collagen or A23187. ADP-induced secretion was highly variable between dogs; however, the kinetics of release was unique and very unusual in thrombopathic platelets. Thrombopathic platelets released their $^{14}$C-serotonin within 30 seconds of ADP addition and the percent released was dose-independent. In contrast, normal dog platelets did not release $^{14}$C-serotonin prior to 1 minute post ADP addition and percent released was dose-dependent. Thrombin induced $^{14}$C-serotonin release was comparable in thrombopathic and normal dog platelets. Thrombopathic platelet alpha granule content of fibrinogen was normal as were membrane glycoproteins IIb and IIIa. Clot retraction assays were also normal. To rule out the possibility that BHT might be a form of variant Glanzmann thrombasthenia, cDNA sequences encoding IIb and IIIa obtained from affected basset hounds were evaluated and found to be identical to sequences observed in normal dogs (Boudreaux, unpublished findings). Thrombopathic platelets were found to have increased basal levels of cAMP as well as impaired cAMP metabolism in experiments using an activator of adenylate cyclase (forskolin) and a phosphodiesterase inhibitor, 1-methyl-3-isobutylxanthine (MIX) (Boudreaux et al 1986a; Boudreaux et al 1986b). Phosphodiesterase activity was normal in platelet extracts suggesting an impairment of regulatory control.

B. Techniques and Results

Platelet-derived cDNA sequences encoding CalDAG-GEFI were evaluated in 2 thrombopathic Basset hounds and one normal mixed-breed dog. Sequences obtained from the thrombopathic Basset hounds and the mixed breed dog matched Boxer dog sequence available on GenBank except for a 3 base pair deletion (TCT) observed at nucleotides 509, 510, and 511 within Exon 5 in samples obtained from thrombopathic Basset hounds. An alternatively spliced segment was also observed in thrombopathic Basset hounds that was not observed in sequence obtained from normal dogs between Exons 1 and 6. The alternatively spliced version included Exon 1 with 27 nucleotides missing near the center of the Exon, Exon 2 was absent, and Exon 3 was present but missing 40 nucleotides from the beginning of the Exon. Exons 4, 5, and 6 were intact except for the missing TCT in Exon 5. Because of frame shift, a premature stop codon appeared within Exon 4. The sequence up to the TGA is: ATG GCG GGC GCT CTG GAC CTG GAC AAG GGC TGC ATC GAA GCC TTC GGT GAA AAC GTG CCA CCT GGT CAG GTA CTG GAT CTC AGC ATT CCC AGC AGA GTT TGA (SEQ ID NO:31).

The predicted translation would be: MAGALDLD-KGCIEAFGENVPPGQVLDLSIPSRV (SEQ ID NO:32).

The significance of this alternatively spliced cDNA sequence is not known. cDNA sequence also revealed a 175 base pair deletion after the $6^{th}$ nucleotide following the stop codon, TAA. This deletion was observed in normal dog and in thrombopathic Basset hounds.

DNA sequences encoding CalDAG-GEFI were evaluated in 57 Basset hounds, 1 Landseer, 1 Eskimo Spitz, 1 mixed-breed dog, and 1 Cavalier King Charles Spaniel. Of the 57 Basset hounds, 8 were affected (identified either with platelet function studies or by ruling out other possible causes of bleeding). One dog was an obligate carrier since it had sired an affected Basset hound.

The Landseer was an obligate carrier for a bleeding disorder described in Landseers in the Netherlands. The Eskimo Spitz was an affected dog with a platelet function disorder essentially identical to that described in Basset hounds (Boudreaux et al 1994). The mixed-breed dog had normal platelet function. The Cavalier King Charles Spaniel had a macrothrombocytopenia and enhanced platelet reactivity in response to ADP and collagen.

DNA sequences encoding the CalDAG-GEFI gene in 41 basset hounds were identical to normal Boxer dog sequence available as part of the dog genome located at NCBI. DNA sequences from the 8 affected Basset hounds were identical as well except for a three base pair deletion (TCT) located at nucleotide positions 509, 510, and 511 in Exon 5. This portion of the gene encodes for the structurally conserved region 1 (SCR1) of the catalytic domain within the protein. This deletion would be predicted to result in the elimination of a highly conserved phenylalanine (amino acid 170) from within the catalytic unit of CalDAG-GEFI. The obligate carrier Basset hound was heterozygous for this deletion as were 6 other Basset hounds who were clinically normal but were highly related to other dogs that had been identified as either being carriers or affected. The other 4, non-Basset dogs were clear of this deletion and matched normal dog genome in this location.

DNA sequence encoding the CalDAG-GEFI gene in the Eskimo Spitz dog with thrombopathia was identical to normal Boxer dog sequence except for a single nucleotide insertion (A) between nucleotides 452 and 453 within Exon 5 at the beginning of the sequence encoding SCR1 of the catalytic domain. This insertion would be predicted to result in a frame shift and encoding of amino acids not compatible with the types of amino acids necessary for the proper function of this protein. Assuming normal splicing, the frame shift would result in the appearance of a premature stop codon near the end of Exon 7.

DNA sequence encoding the CalDAG-GEFI gene in the obligate carrier Landseer was identical to normal boxer dog sequence except for a heterozygous nucleotide substitution of a T for a C at nucleotide position 982 in Exon 8. This mutation in the homozygous state would be predicted to result in the substitution of a premature stop codon in the place of an arginine at amino acid position 328 within structurally conserved region 4 (SCR4) of the catalytic unit. This would greatly impair the function and/or synthesis of the protein. Six other Landseer samples were subsequently evaluated, one from an obligate carrier, one from an affected dog, and 4 from dogs of unknown status but highly related to the obligate carriers and not clinical bleeders. The obligate carrier and 3 of the Landseers of unknown status were found to be heterozygous for the mutation. One Landseer of unknown status was found to be clear of the mutation (identical to normal dog). The affected Landseer was found to be homozygous for the mutation. DNA samples obtained from a Landseer seen at Auburn University as well as from a Great Pyrenees heterozygous for Glanzmann thrombasthenia, were found to match dog genome at this location.

DNA sequence encoding the CalDAG-GEFI gene in the Cavalier King Charles Spaniel was identical to normal Boxer dog sequence except for minor polymorphisms that did not result in a change in encoded amino acids. DNA sequence encoding the CalDAG-GEFI gene in the normal mixed-breed dog matched normal Boxer dog sequence.

The intron polymorphisms included:
Intron 1—complete—none seen
Intron 2—complete—c to g at 326; a to t at 413 in mix, Landseer, CKCS. tttttttttctttttt (SEQ ID NO:33) starting at position 490 had variation in mix, Landseer, CKCS.
Intron 3—complete—none seen
Intron 4—partial—none seen
Intron 5—complete—a to g at 70; g deletion at 96 in mix (heterozygous for g deletion), Landseer (heterozygous for g deletion), CKCS.
Intron 6—complete—none seen
Intron 7—partial—none seen
Intron 8—partial—none seen
Intron 9—complete—none seen
Intron 10-complete—none seen
Intron 11—partial—c to t at −18 from beginning of exon 12; c to t at −26 from beginning of exon 12 in mix.
Intron 12—complete—c to a at 34 in mix (heterozygous)
Intron 13—complete—gg deletion at 75, 76 in Landseer; gggggggggagggc (SEQ ID NO:34) replaced with ggtggtggtggggggg (SEQ ID NO:35) at 261 to 274 in Landseer.
Intron 14—partial—none seen
UTR—175 bp "intron" spliced out in normal dogs and bassets. g to a at 19 of UTR intron in Landseer (heterozygous); also insertion/deletion near end of UTR intron in Landseer (heterozygous).

Structurally Conserved Regions (SCR) within the catalytic unit (Quilliam et al., PROG. NUC. ACID RES. MOL. BIOL. 71:391-444 (2002), incorporated by reference herein in its entirety):

Landseers with Thrombopathia have a premature stop codon at the codon encoding arginine (R; amino acid 328) due to a substitution of a T for a C at nucleotide 982 at the beginning of the sequence encoding SCR4.

C. Summary

Three distinct mutations were identified in the gene encoding CalDAG-GEFI, a guanine nucleotide exchange factor found in platelets that is critically important for normal platelet function. These mutations were all located within regions of the gene encoding structurally conserved regions within the catalytic domain of the protein. As a result of these mutation, affected dogs experienced platelet dysfunction and abnormal bleeding tendencies. CalDAG-GEFI has profound significance in terms of biological function of platelets. This protein is involved in signal transduction events that are important for inside-out as well as outside-in integrin signaling events. The protein also plays an important role in regulating the platelet release reaction and likely plays a role in cAMP metabolism and phosphodiesterase regulation, Drugs that inhibit this protein will impair platelet function by impacting on the roles this protein plays in platelet signal transduction events. Over-expression of this protein has also been associated with myeloid leukemia in a mouse model. Therefore this protein may be implicated in certain types of cancer.

D. Methods cDNA—Platelet-rich plasma (PRP) was isolated from EDTA-anticoagulated blood using differential centrifugation. Prostaglandin E1 was added to PRP samples at a final concentration of 3 µM prior to centrifugation of PRP to form pellets. Platelet pellets were resuspended in a small volume of autologous plasma and transferred to RNase-free tubes and centrifuged again. Residual plasma was removed from the pellets and the pellets were frozen at −80 degrees C. until used later for RNA isolation. Total RNA was isolated from platelet pellets using a commercially available kit (Micro to Midi Total RNA Purification Kit, Invitrogen). cDNA synthesis was accomplished using a separate commercially available kit (iScript cDNA synthesis kit, Bio-Rad). Genomic DNA was harvested from EDTA-anticoagulated whole blood using a commercially available kit (QIAamp DNA Blood Mini Kit, Qiagen, Inc., Valencia, Calif.). Primers were designed based on sequence information found on GenBank (GI:73983733, PREDICTED: *Canis familiaris* sequence similar to RAS guanyl releasing protein 2 isoform 1, mRNA) and sequence

```
SCR1 = FDHLEPLELAEHLTYLEYRSFCKI                         (SEQ ID NO: 26)

SCR2 = RALVITHFVHVAEKLLHLQNFNTLMAVVGGLSHSSISRLKETH      (SEQ ID NO: 27)

SCR3 = GFRFPILGVHLKDLVALQLALPD                          (SEQ ID NO: 28)

SCR4 = RLNGAK                                           (SEQ ID NO: 29)

SCR5 = LYQLSLQREPR                                      (SEQ ID NO: 30)
```

Bassets with Throbopathia are missing the phenylalanine (F; amino acid 170) in SCR1. This is due to a deletion in nucleotides 509, 510, and 511.

Eskimo Spitz with Thrombopathia have an insertion (A) between nucleotides 452 and 453 resulting in a frame shift starting at the codon encoding aspartic acid, (D; amino acid 151) at the beginning of SCR1. In the sequence, the frame-shifted sequence includes a stop codon in Exon 7.

within the dog genome located using mRNA sequence information. DNA segments were amplified by polymerase chain reaction (PCR) by using normal canine DNA as a template initially. Amplification products were separated on agarose gels using electrophoresis. DNA was extracted from target bands using a commercially available kit (QIAquick Gel Extraction Kit, Qiagen, Inc., Valencia, Calif.). Extracted DNA was submitted for DNA sequencing in a laboratory equipped with an ABI 3100 Genetic Analyzer.

Example II

Calcium-Diacylglycerol Guanine Nucleotide Exchange Factor I Gene Mutations Associated with Loss of Function in Canine Platelets A. Introduction Reference is made to Boudreax et al., Translation Res. 150:81-92 (2007), which is incorporated by reference herein in its entirety. Calcium-Diacylglycerol Guanine Nucleotide Exchange Factor I (CalDAG-GEFI) has been implicated in platelet aggregation signaling in CalDAG-GEFI knockouts. Functional mutations were identified in the gene encoding for CalDAG-GEFI in 3 dog breeds. Affected dogs experienced epistaxis, gingival bleeding, and petechiation. Platelet number, von Willebrand factor, clot retraction, and coagulation screening assays were normal, whereas bleeding time tests were prolonged. Platelet aggregation and release responses to all agonists, except thrombin, were markedly impaired. Platelet membranes had normal concentrations of integrin alphaIIb-beta3; however, ADP-induced fibrinogen binding by activated platelets was markedly impaired. Forskolin-stimulated platelets exhibited a marked increase in intraplatelet cAMP associated with impaired phosphodiesterase (PDE) activity, whereas levels of extractable phosphoinositides were 1.5-fold to 2-fold higher in thrombin-stimulated affected platelets. DNA analysis of the CalDAG-GEFI gene in affected dogs documented the existence of 3 distinct mutations within portions of the CalDAG-GEFI gene encoding for structurally conserved regions within the catalytic domain of the protein. The mutations are predicted to result in either lack of synthesis, enhanced degradation, or marked impairment of protein function. The dysfunctional profile of canine platelets observed in mutant dogs putatively links CalDAG-GEFI and its target Rap1 or other Ras family member, for the first time, to a role in pathways that regulate cAMP PDE activity and thrombin-stimulated phosphoinositide anchoring or metabolism. The finding of distinct functional mutations in 3 dog breeds suggests that mutations in the CalDAG-GEFI gene may be implicated in similar defects in human patients with congenital platelet disorders having primary secretion defects of unknown etiology.

B. Materials and Methods

This study was conducted in compliance with ethical guidelines for research involving the use of animals.

1. cDNA Synthesis

Platelet rich plasma (PRP) was isolated from ethylenediaminetetraacetic acid (EDTA)-anticoagulated blood using differential centrifugation. Prostaglandin E1 was added to PRP samples at a final concentration of 3 µM before centrifugation of PRP to form pellets. Platelet pellets were resuspended in a small volume of autologous plasma and transferred to RNase-free tubes and centrifuged again. Residual plasma was removed from the pellets, and the pellets were frozen at −80° C. until use for RNA isolation. Total RNA was isolated from platelet pellets using a commercially available kit (Micro to Midi Total RNA Purification Kit; Invitrogen, Carlsbad, Calif.). cDNA synthesis was accomplished using a separate commercially available kit (iScript cDNA synthesis kit; BioRad, Hercules, Calif.).

2. Genomic DNA Isolation

Genomic DNA was harvested from EDTA-anticoagulated whole blood using a commercially available kit (QIAamp DNA Blood Mini Kit; Qiagen, Valencia, Calif.).

3. Polymerase Chain Reaction (PCR) Analysis

Primers for CalDAG-GEFI were designed based on sequence information found on GenBank (GI:73983733, PREDICTED: *Canis familiaris* sequence similar to RAS guanyl releasing protein 2 isoform 1, mRNA) and sequence within the dog genome located using mRNA sequence information (FIG. 1). Primers for protease activated receptor (PAR) 1, PAR3, and PAR4 were designed based on human and mouse sequences located on GenBank. cDNA and DNA segments were initially amplified by PCR by using normal canine cDNA or DNA as a template. Amplification products were separated on agarose gels using electrophoresis. DNA was extracted from target bands using a commercially available kit (QIAquick Gel Extraction Kit; Qiagen). Extracted DNA was submitted for DNA sequencing in a laboratory equipped with an ABI 3100 Genetic Analyzer.

4. Flow Cytometry

Citrated PRP (10 µL) was added to 100 µL of flow buffer (10 mM HEPES, 145 mM NaCl, 5 mM KCl, 1 mM $MgSO_4$, pH 7.4) in round-bottomed polystyrene tubes. Monoclonal antibodies were added directly to samples of diluted PRP. Monoclonal antibodies evaluated included Y2/51, an FITC-labeled antibody against human platelet glycoprotein IIIa (DAKO, Carpinteria, Calif.) that recognizes canine IIIa, 2F9 a monoclonal antibody recognizing canine IIb (kind gift from Dr. S. A. Burstein, University of Oklahoma Health Sciences Center), and canine activated platelet-1 (CAP-1), a monoclonal antibody recognizing a receptor induced binding site (RIBS) on canine fibrinogen (M. K. Boudreaux et al., Vet Pathol 33: 419-4270 (1996). The FITC-labeled isotype control antibody was used for samples evaluating binding of Y2/51. CAP-1 binding was evaluated using a secondary, FITC-labeled antibody, which was also used without primary antibody in control experiments to detect nonspecific binding. CAP-1 binding was evaluated in nonactivated and activated PRP samples. Samples were fixed with 500 µL of 2% formalin and immediately evaluated by flow cytometry (Coulter Epics Elite, Hialeah, Fla.).

5. Sodium Dodecyl Sulfate Polyacrylamide Gel Electrophoresis (SDS-PAGE) and Western Blot Analysis Human and canine blood was collected into ACD-A, and platelets were isolated essentially as described for phospholipid analysis (M. B. Brooks et al., Blood 99:2434-2441 (2002)). After the second wash, platelets were resuspended to a final concentration of $3 \times 10^8$ platelets per 1.0 mL wash buffer and 2, 10-µL aliquots were removed for protein determination (BCA Protein Assay Reagent Kit; Pierce Biotechnology, Rockford, Ill.). The remaining cell suspension was recentrifuged. The supernatants were discarded, and platelet pellets were stored frozen at −70° C. until analysis. The frozen platelet pellets were lysed in hot (95° C.) Laemelli SDS-PAGE sample buffer (BioRad) with vortex mixing and heated for 4 min at 95° C. Platelet proteins were separated by SDS-PAGE on 12.5% polyacrylamide gels (Ready Gels, Bio-Rad) with 40-µg protein loaded per lane and then electroblotted onto PVDF membranes (BioRad) using cooled Tris-glycine buffer (25 mM Tris, pH 8.3, 192 mM glycine). The PVDF membranes were then blocked overnight at 4-8° C. using 5% (wt/vol) powdered milk in TBS-T (20 mM Tris HCL, pH 7.5, 500 mM NaCl, 0.1% (wt/vol) Tween-20). The blots were washed 3 times in TBS-T and probed for 1 h at 18-24° C. using a purified mouse monoclonal antibody (MO9, clone 3D8, Abnova Corporation, Taipei, Taiwan) that recognizes a partial recombinant human RasGRP2 (CalDAG-GEFI) protein. The sequence of the recombinant human protein is homologous with canine sequence for CalDAG-GEFI. The antibody was diluted to 1 µg per mL in TBS-T and reacted with immunoblots for 1 h at 18-24° C. The blots were also probed with a rabbit anti-human Rap1 polyclonal antibody (Stressgen Bioreagents, Victoria, British Columbia, Canada)

with cross reactivity to canine Rap1. After incubation with primary antibodies, the blots were washed 3 times in TBS-T, reacted for 1 h at 18-24° C. with either purified goat anti-mouse or purified goat anti-rabbit IgG conjugated to HRP (BioRad) diluted 1:50,000 in TBS-T, and then washed 3 times in TBS-T. Immunoreactive protein bands were visualized using the ECL-Plus Western Blotting Detection System (GE Healthcare, Chalfont St. Giles, United Kingdom) and high-performance chemiluminescence film (Hyperfilm ECL; Amersham Biosciences, Piscataway, N.J.) according to manufacturer suggested protocols. Films were scanned using standard imaging software (Adobe Photoshop v.7.0.1; Adobe Corporation, San Jose, Calif.).

6. Platelet Phosphoinositides

Platelets from normal dogs and affected Basset hounds were labeled with [$^3$H]-inositol essentially as detailed by Huang (E. M. Huang and T. C. Detwiler, Biochem J 242:11-18 (1987)). Radiolabeled platelets were activated by addition of either saline (0.15 M NaCl) or 1 Unit/mL human alpha-thrombin at 37° C., with stirring at 950 RPM for various times from 0 s to 120 s. Reactions were terminated by rapid addition of ice cold 10% (vol/vol) HClO$_4$ and extracted as detailed by Wreggett (K. A. Wreggett et al., Biochem J 245:933-934 (1987)) with inclusion of phytate hydrolysate to optimize recovery. [$^3$H]-labeled inositol phosphates were separated using QMA anion exchange SEP-PAKS (Waters Corp, Milford, Mass.) and ammonium formate buffers (K. A. Wreggett and R. F. Irvine, Biochem J 245:655-660 (1987)).

C. Results

1. Flow Cytometry

Monoclonal antibody Y2/51, recognizing platelet glycoprotein IIIa, bound normally to platelets obtained from affected Basset hounds and Spitz dogs (M. K. Boudreaux et al., J Vet Int Med 8: 93-98 (1994)) in contrast to platelets obtained from dogs with Glanzmann thrombasthenia (GT) in which binding was markedly reduced (M. K. Boudreaux et al., Vet Pathol 33:503-511 (1996)). CAP-1, a monoclonal antibody that recognizes a RIBS on canine fibrinogen, did not bind significantly to nonactivated platelets obtained from either normal dogs or dogs with Basset hound thrombopathia or GT (M. K. Boudreaux et al., Vet Pathol 33:503-511 (1996)) (Spitz dog platelets were not available for CAP-1 flow cytometry studies.) Platelets obtained from normal dogs and activated with ADP or PAF bound CAP-1 in a dose-dependent fashion. In contrast, platelets obtained from thrombopathic Basset hounds failed to bind CAP-1 even when activated with ADP concentrations as high as 100 µM (FIG. 2). Platelets from dogs with GT also failed to bind CAP-1.

2. CalDAG-GEFI cDNA and DNA Sequences

Platelet-derived cDNA sequences encoding CalDAG-GEFI were evaluated in 2 thrombopathic Basset hounds and 1 normal mixed-breed dog. Sequences obtained from the thrombopathic Basset hounds and the mixed-breed dog matched the Boxer dog sequence available on GenBank except for a 3 base pair deletion (TCT) observed at nucleotides 509, 510, and 511 within Exon 5 (509, 510, 511 delTCT) in samples obtained from thrombopathic Basset hounds (FIG. 3). Alternatively spliced segments were also observed in cDNA samples from thrombopathic Basset hounds and in normal dogs between Exons 1 and 6. Alternatively spliced versions included portions of Exon 1 and Exon 3 with complete deletion of Exon 2. Exons 4, 5, and 6 within these cDNA sequences were complete except for the missing TCT in Exon 5 noted in samples from thrombopathic Basset hounds. Because of frame shift, premature stop codons appeared within the sequences. The significance of these alternatively spliced cDNA sequences is not known. Unusual 5' and 3' splice sites were noted for the intron following Exon 2 (au and ac), which may have contributed to the alternative splicing variations observed. cDNA sequences also revealed a 175 base pair deletion, likely an intron, after the 6th nucleotide following the stop codon, TAA. This deletion was observed in samples from normal dog and from thrombopathic Basset hounds. DNA sequences encoding CalDAG-GEFI were evaluated in 79 Basset hounds, 1 Eskimo Spitz, 8 Landseers, 1 mixed-breed dog, and 1 Cavalier King Charles Spaniel. Of the 79 Basset hounds, 8 were affected (identified either with platelet function studies or by ruling out other possible causes of bleeding). One dog was an obligate carrier and had sired 1 affected dog mentioned above. Platelet function was evaluated in 23 of the remaining Basset hounds, and studies indicated that they either had normal platelet function or slightly reduced platelet function in response to either low doses of ADP, collagen, or both. Platelet function studies were not performed on the remaining Basset hounds who were all reported to be clinically normal. The Eskimo Spitz was an affected dog with a platelet function disorder essentially identical to that described in Basset hounds (J. L. Catalfamo et al., Blood 67:1568-1577 (1986)). Two Landseers were obligate carriers for a bleeding disorder in Landseer in the Netherlands. One Landseers was affected. The remaining 5 Landseers were clinically normal, and 4 were closely related to the affected and obligate carrier Landseers. The mixed-breed dog was clinically normal and had normal platelet function. The Cavalier King Charles Spaniel was clinically normal and had a macro-thrombocytopenia and enhanced platelet reactivity in response to ADP and collagen. DNA sequences for the coding portions of the CalDAG-GEFI gene in 62 Basset hounds were identical to the normal Boxer dog sequence available as part of the dog genome located at NCBI. DNA sequences from the 8 affected Basset hounds were also identical except for a 3 base pair deletion (509, 510, 511 delTCT) located in Exon 5 (FIG. 3). This portion of the gene encodes for the structurally conserved region 1 (SCR 1) of the catalytic domain within the protein (L. A. Quilliam et al., Prog Nuc Acid Res Mol Biol 71L391-444 (2002)). This deletion would be predicted to result in the elimination of a highly conserved phenylalanine (amino acid 170) from within the catalytic unit of CalDAG-GEFI. The obligate carrier Basset hound was heterozygous for this deletion as were 8 other Basset hounds who were clinically normal but were related to other dogs that had been identified as either being carriers or affected. The other 11, non-Basset dogs were clear of this deletion and matched normal dog genome in this location.

The DNA sequence for the coding region of the CalDAG-GEFI gene in the Eskimo Spitz dog with thrombopathia was identical to the normal Boxer dog sequence except for a single nucleotide insertion (A) between nucleotides 452 and 453 within Exon 5 (452-453insA) at the beginning of the sequence encoding SCR1 of the catalytic domain (FIG. 3). This insertion would be predicted to result in a frame shift and encoding of amino acids not compatible with the types of amino acids necessary for the proper function of this protein. Assuming normal splicing, the frame shift would result in the appearance of a premature stop codon near the end of Exon 7. cDNA was not available for evaluation in the affected Spitz. The DNA sequence for the coding region of the CalDAG-GEFI gene in the affected Landseer was identical to the normal Boxer dog sequence except for a nucleotide substitution of T for C at nucleotide position 982 within Exon 8 (982C>T) (FIG. 3). This mutation would be predicted to result in the substitution of a premature stop codon in the place of an arginine at amino acid position 328 (R328Stop)

within SCR4 of the catalytic unit. This result would greatly impair the function and/or synthesis of the protein. The 2 obligate carrier Landseers were identical to the normal Boxer dog sequence except they were heterozygous for the change described in the affected Landseer. Of the remaining 5 Landseers, 3 were found to be heterozygous for the mutation and 2 were found to match normal dog genome. DNA sequence from a Great Pyrenees dog heterozygous for GT was found to match dog genome at this location. This sequence was evaluated because the Landseer breed was derived from the Great Pyrenees as well as the Newfoundland breed. The DNA sequence for the coding region of the CalDAG-GEFI gene in the Cavalier King Charles Spaniel was identical to the normal Boxer dog sequence except for minor polymorphisms that did not result in a change in encoded amino acids. DNA sequences for the coding region of the CalDAG-GEFI gene in the normal mixed-breed dog matched the normal Boxer dog sequence.

3. CalDAG-GEFI Expression

Figure 4:
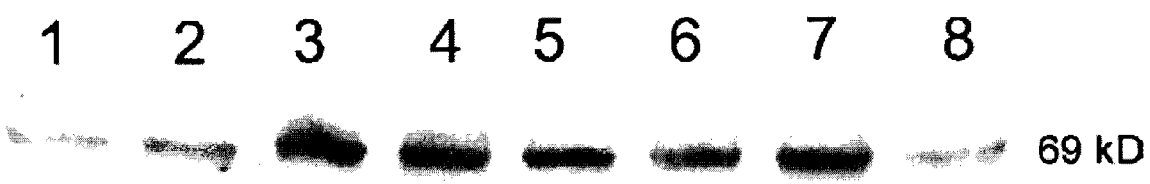
FIG. 4 displays a Western blot analysis of CalDAG-GEFI in platelet lysates from normal dogs and affected Basset hounds. Each lane was loaded with 40-µg total protein. Lanes 1 and 8=human, lanes 2 and 6=normal dog, lanes 3 and 7=affected Basset hound 1, lane 4=affected Basset hound 2, and lane 6=affected Basset hound 3. Canine platelet CalDAG-GEFI was detected using murine monoclonal antibody MO9, clone 3D8 to partial recombinant human RasGRP2 (CalDAG-GEFI).

Platelet extracts were evaluated for the presence of CalDAG-GEFI using SDS-PAGE and Western blotting. A murine monoclonal antibody to human CalDAG-GEFI recombinant protein sequence reacted with a protein band at 69 kD that corresponds to the predicted size for CalDAG-GEFI. Platelet extracts from human (n=1), dog (n=2), and affected Basset hounds (n=3) had comparative levels of reactive protein (FIG. 4). The blot was also probed for Rap1 using a rabbit polyclonal antibody to human Rap1 with cross reactivity to canine Rap1. Similar amounts of Rap1 were detected in platelet lysates from human, normal dogs, and affected Basset hounds. (Data not shown.) These results demonstrate the expression of CalDAG-GEFI in affected Basset hound platelets and suggest that the mutant protein is dysfunctional. No evidence for enhanced proteolysis of the mutant form of canine CalDAG-GEFI was observed. Platelet lysates were not available from Eskimo Spitz or Landseers; however, in light of their mutations, which result in the appearance of premature stop codons, one could speculate that protein synthesis of platelet CalDAG-GEFI does not occur in those disorders.

4. PAR1, PAR3, and PAR4 cDNA Sequences

Information concerning PAR receptors on canine platelets has not been published, and it is not known whether canine platelets possess PAR1, PAR3, and/or PAR4 receptors similar to those documented in mice and people. This information coupled with the importance of PAR signaling in thrombin mediated platelet activation and the impaired reactivity to thrombin of platelets from dogs with the mutations prompted an evaluation of canine PAR encoding sequences. cDNA sequences encoding PAR1, PAR3, and PAR4 were amplified from cDNA obtained from normal dog platelets and compared with normal human and mouse sequence information. The sequences encoding the cleavage regions of the tethered thrombin receptor activation peptides (TRAPs) suggested that dog platelets do synthesize these 3 receptors similarly to those reported for mouse and human platelets. Encoded amino acids were similar but not identical to either human or mouse platelet receptors (FIG. 5). PAR1 cDNA encoded for 2 additional amino acids 15 amino acids beyond the predicted cleavage site that were not present in human sequence. The first 23 amino acids of the predicted tethered ligands for PAR1, PAR3, and PAR4 in dogs were

SFFLKNTNDGFEPFPLEEDEEKN, (SEQ ID NO: 36)

TFRGAPSNSFEEFPLSAIEGWTE, (SEQ ID NO: 37)
and

SFPGQPWANNSDILEIPESSRAL, respectively. (SEQ ID NO: 38)

5. Inositol Phosphates

An inherited human bleeding disorder has been identified in association with defective initial platelet reactivity and impaired platelet phosphatidylinositol metabolism (B. Lages and H. J. Weiss, Thromb Haemost 59:175-179 (1988)). Affected Basset hound platelets exhibited impaired initial platelet reactivity to thrombin, we examined thrombin-stimulated phosphoinositide hydrolysis in normal dogs and affected Basset hounds. Similar levels of radiolabeled $IP_1$, $IP_2$, $IP_3$, and $IP_4$ were extracted after 120 s from unstimulated saline control platelets evaluated in normal and affected dogs. At 120 s, levels of $IP_1$, $IP_2$, $IP_3$, and $IP_4$ were 1342, 1300; 497, 390; 226, 260 and 226, 236 [$^3$H] dpm/$10^9$ platelets for normal and affected dogs, respectively. In contrast, at all time points, postthrombin activation (5, 10, 15, 30, and 120 s) IP extracts from affected platelets were 1.5-fold to 2-fold higher, with peak thrombin-stimulated accumulation at 120 s. $IP_1$, $IP_2$, $IP_3$, and $IP_4$ levels at 120 s postthrombin stimulation were 2787, 5390; 2558, 2830; 557, 873 and 180, 378 [$^3$H] dpm/$10^9$ platelets from normal and affected dogs, respectively.

D. Discussion

Figure 6:
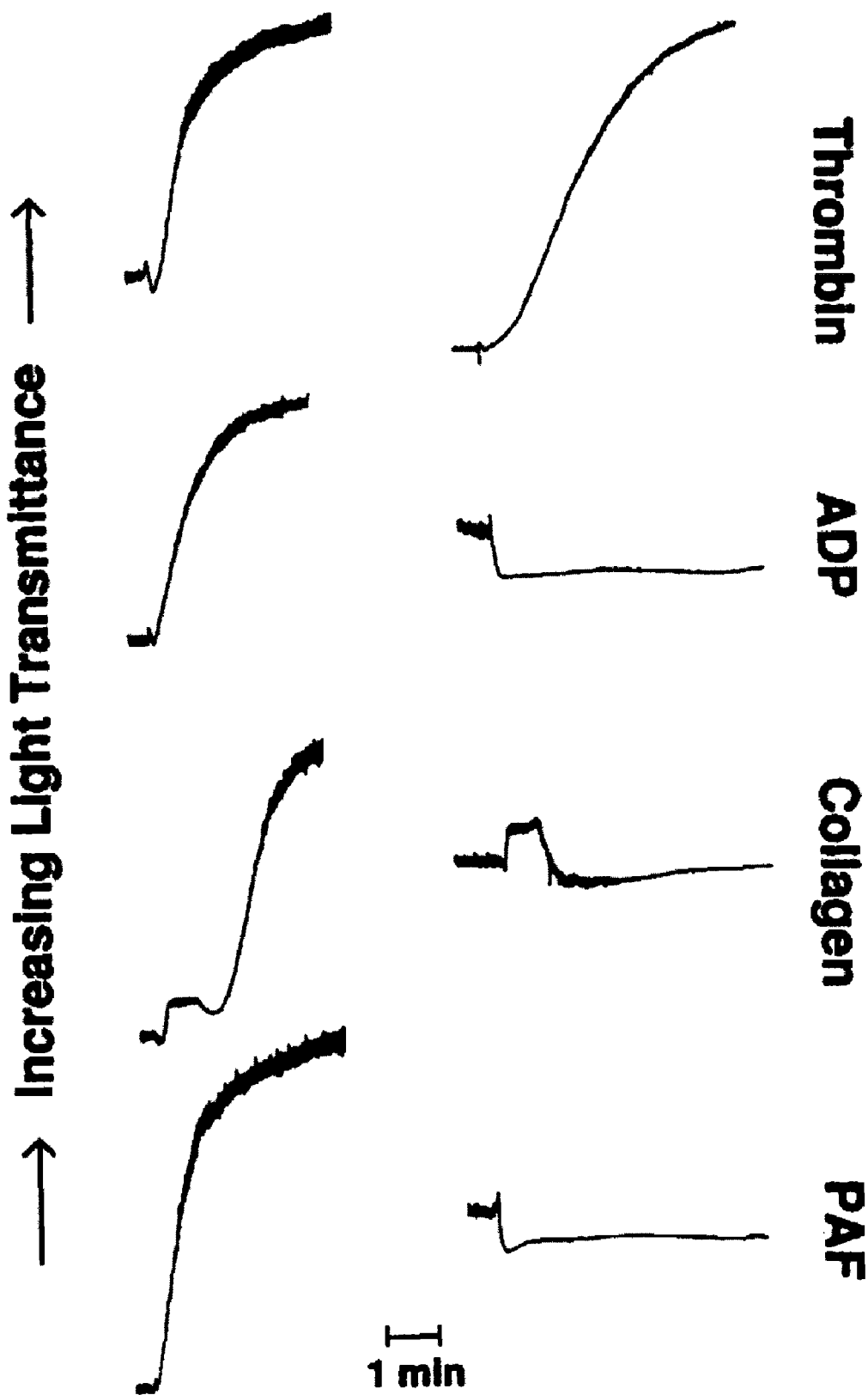
FIG. 6 displays representative aggregation tracings from Basset hounds or Spitz dogs with thrombopathia compared with normal dogs. Aggregation responses in affected dogs are markedly impaired at all concentrations of agonists used. Thrombopathic platelets respond to thrombin with a characteristic lag phase. Reprinted with permission from Boudreaux et al (M. K. Boudreaux et al., J Vet Int Med 8:93-98 (1994), pp. 93-98)

Inherited platelet function disorders in Basset hounds and Spitz dogs have been reported previously (I. B. Johnstone and F. Lotz, Can Vet J 20:211-215 (1979); J. L. Catalfamo et al., Blood 67:1568-1577 (1986); M. K. Boudreaux et al., J Vet Int Med 8:93-98 (1994)). Platelet aggregation responses of affected Basset hounds and Spitz dogs are essentially identical and are characterized by normal shape change responses but markedly impaired aggregation responses to ADP, collagen, calcium ionophore A23187, and PAF. In both disorders, the thrombin response is delayed with maximal aggregation occurring in approximately 5 min to 6 min instead of the typical 2-min to 3-min maximum response observed with normal canine platelets (FIG. 6). Clot retraction is normal in both disorders. Dense granule secretion as demonstrated using $^{14}$C-serotonin release is markedly impaired in thrombopathic platelets obtained from Basset hounds and Spitz dogs (J. L. Catalfamo et al., Blood 67:1568-1577 (1986); M. K. Boudreaux et al., J Vet Int Med 8:93-98 (1994)). Although uptake of serotonin is normal, thrombopathic platelets release less than 6% of their total platelet $^{14}$C-serotonin in response to collagen or A23187. ADP-induced secretion is highly variable between dogs; however, the kinetics of release is unique and very unusual in thrombopathic platelets obtained from Basset hounds. Thrombopathic platelets release their $^{14}$C-serotonin within 30 s of ADP addition, and the percent released is dose-independent. In contrast, normal dog platelets do not release $^{14}$C-serotonin before 1-min post-ADP addition and percent release is dose-dependent. Thrombin-induced $^{14}$C-serotonin release is comparable in thrombopathic and normal dog platelets.

In earlier studies, thrombopathic Basset hound platelets were found to have increased basal levels of cAMP as well as impaired cAMP metabolism in experiments using an activator of adenylate cyclase (forskolin) and a phosphodiesterase (PDE) inhibitor, 1-methyl-3-isobutylxanthine (M. K. Boudreaux et al., Biochem Biophys Res Commun 140:589-594

(1986); M. K. Boudreaux et al., Biochem Biophys Res Commun 140:595-601 (1986)). PDE activity was normal in platelet extracts, which suggested an impairment of regulatory control. Platelets from affected Basset hounds also exhibited increased levels of extractable phosphoinositides when stimulated with thrombin, which suggested either differences in phosphoinositide metabolic pathways or differences in PI anchoring and recovery. These findings suggest a putative link between CalDAG-GEFI and its target Rap1 or an unrecognized target Ras involved in pathways that regulate cAMP PDE activity and thrombin-stimulated phosphoinositide anchoring or metabolism. In this study, 3 distinct mutations were identified in 3 different breeds of dogs in the gene encoding CalDAG-GEFI, a guanine nucleotide exchange factor found in platelets that is critically important for normal platelet function. These mutations were all located within regions of the gene encoding structurally conserved regions within the catalytic domain of the protein. In affected Basset hounds, Western blots of platelet lysates indicated that CalDAG-GEFI levels were similar to normal dogs, which suggests that this mutation results in expression of a protein that seems to be functionally impaired.

The 3 distinct mutations identified in affected dogs are associated with profound platelet dysfunction and abnormal bleeding tendencies that parallel those recently reported for CalDAG-GEFI knockout mice (Table 1). The significance of CalDAG-GEFI function was demonstrated in studies with megakaryocytes that did not have the transcription factor NF-E2. NF-E2$^{-/-}$ megakaryocytes could not undergo agonist-induced fibrinogen binding (M. Shiraga et al., J Cell Biol 147:1419-1430 (1999)) because of the absence of the gene encoding CalDAG-GEFI (H. Kawasaki et al., Proc Natl Acad Sci USA 95:13278-13283 (1998)). Forced expression of CalDAG-GEFI in these megakaryocytes led to enhanced agonist-induced binding of fibrinogen to alphaIIb-beta3 (K. Eto et al., Proc Natl Acad Sci USA 99:12819-12824 (2002)). CalDAG-GEFI contains 4 major domain structures including (1) Ras exchanger motif domain common to Ras family GEFs; (2) cdc25-like GEF (catalytic) domain; (3) 2 EF hand domains for interaction with calcium; and (4) C1 domain for interaction with DAG and phorbol esters (K. Eto et al., Proc Natl Acad Sci USA 99:12819-12824 (2002)). The catalytic domain of CalDAG-GEFI is critically important for the GEF-mediated activation of Rap1b.

Table 1. Comparative phenotype data for CalDAG-GEFI knockout mice and dogs homozygous for CalDAG-GEFI gene mutations

| TESTS | CalDAG-GEFI knockout mice | CalDAG-GEFI gene mutations (dogs) |
|---|---|---|
| Platelet number | normal | normal |
| Bleeding time | markedly prolonged | markedly prolonged |
| Coagulation assays | normal | normal |
| Intraplatelet/plasma fibrinogen | not evaluated | normal |
| von Willebrand factor | not evaluated | normal |
| Tether to a collagen surface | normal | normal |
| Firmly anchor to a collagen surface | impaired | impaired* |
| Platelet function: | | |
| Shape change (all tested agonists) | normal | normal |
| Aggregation: | | |
| ADP, 2-10 uM | absent | absent |
| ADP, >50 uM | absent | absent; occasional microaggregates |
| Collagen, >20 ug/uL | absent | absent |
| alpha thrombin, 0.1 U/mL | rate and max extent impaired | rate and max extent impaired |
| alpha thrombin, 1.0 U/mL | rate and max extent normal | rate impaired, max extent normal |
| gamma thrombin, 16 nM | not evaluated | rate impaired, max extent normal |
| Calcium Ionophore A23187 | | |
| 5-10 uM in PRP | absent | absent |
| 5-10 uM in GFP + 1 mM Ca2+ | not evaluated | rate impaired, max extent normal |
| U46619 or Na Arachidonate | impaired | impaired |
| PMA, 1.5-3 uM | normal | normal |
| Adenine nucleotide content | not evaluated | normal |
| Granule secretion | | |
| ADP, 10 to 100 uM | not evaluated | atypical |
| Collagen, 12-100 ug/mL or CRP 1-50 ug/mL | impaired | impaired |
| alpha thrombin, 0.1 U/mL | normal | normal |
| alpha thrombin, 1.0 U/mL | normal | normal |
| aIIbβ3 integrin concentration | normal | normal |
| aIIbβ3 integrin activation | | |
| ADP, 10 to 100 uM | not evaluated | impaired |
| Collagen, 12 to 100 ug/mL or CRP 1-50 ug/mL | impaired | impaired |
| alpha thrombin, 0.1 U/mL | normal | impaired |
| alpha thrombin, 1.0 U/mL | not evaluated | normal |
| Calcium Ionophore A23187, 1 uM | not evaluated | impaired |
| Calcium Ionophore A23187, 10 uM | not evaluated | normal |
| Clot retraction | not evaluated | normal |

| TESTS | CalDAG-GEFI knockout mice | CalDAG-GEFI gene mutations (dogs) |
|---|---|---|
| Intraplatelet cAMP | | |
| Resting, unstimulated | not evaluated | slightly elevated |
| Forskolin stimulated | not evaluated | markedly elevated |
| cAMP PDE activity, regulatory control | not evaluated | impaired |
| Extractable phosphoinositides | | |
| alpha thrombin, 1.0 U | not evaluated | elevated |

*Prolonged collagen-induced thrombus formation (Clot signature analyzer, unpublished data).

Thrombopathic platelets undergo normal clot retraction and respond fully to thrombin although with impaired kinetics. PARs have not been characterized on canine platelets. In a comparative study, dog platelets were found to be nonresponsive to SFLLRN (SEQ ID NO:39) (J. L. Catalfamo et al., Thromb Haemost 69:1195 (1993); C. K. Derian et al., Thromb Res 78:505-519 (1995)). This nonresponsiveness may have been from use of the nonspecific peptide for dog platelets (SFLLRN (SEQ ID NO:39) instead of SFFLKN (SEQ ID NO:40)) or from reduced affinity of binding of soluble TRAPs to canine PAR receptors on platelets. The possibility of the latter is suggested by parallel dose response curves obtained for platelet activation of canine or human platelets by human alpha thrombin J. L. Catalfamo et al., Blood 67: 1568-1577 (1986)) and human gamma thrombin (Catalfamo, unpublished data), which has been reported to selectively activate PAR4 (G. Soslau et al., Platelets 15:155-166 (2004)).

Our evaluation of dog platelet cDNA sequences suggests that dog platelets do possess PAR1, PAR3, and PAR4 receptors. Biphasic kinetics of activation and signaling for PAR1 and PAR4 have been described for human platelets (L. Covic et al., Biochem 39:5458-5467 (2000)). In that study, PAR1 binding resulted in a rapid spike in calcium influx followed by a PAR4-induced slower and prolonged calcium influx. PAR4 was found to generate a sustained calcium signal and was considered to be more effective than PAR1 in eliciting secondary autocrine signals necessary for complete platelet activation. The delayed kinetics of thrombin activation observed in thrombopathic canine platelets may be mediated by PAR4 signaling. This result suggests that PAR1 signaling may require CalDAG-GEFI activation of Rap1b, whereas PAR4 signaling does not. Thrombin has been shown to activate Rap1b in 2 phases, with the second phase being mediated via protein kinase C(PKC) (B. Franke et al., Mol Cell Biol 20: 779-785 (2000)). Phorbol myristate acetate, an activator of PKC, has been shown to activate platelets of thrombopathic Basset hounds in a manner similar to normal canine platelets (M. F. McConnell et al., Platelets 6:131-145 (1995)). These findings suggest that thrombin signaling through PAR4 is linked to activation of PKC with resulting activation of Rap1b in a manner independent of CalDAG-GEFI. Thrombin-induced serotonin release kinetics were rapid and normal in thrombopathic platelets, which rules out delayed dense granule release of ADP as a reason for the delay in thrombin-induced platelet aggregation. Thrombopathic platelets did not bind CAP-1, a monoclonal antibody to a RIBS epitope on canine fibrinogen, in response to ADP or PAF, even at high agonist concentrations.

In an earlier study (W. R. Patterson et al, Thromb Haemost 62:1011-1015 (1989)), thrombopathic platelets were found to bind soluble fibrinogen in the absence of platelet aggregation. In that study it is likely that the form of fibrinogen detected on platelet surfaces had not undergone the conformational change induced by binding to the alphaIIb-beta3 integrin receptor that is detected by CAP-1. Interestingly, thrombopathic platelets do form micro-aggregates in the presence of high concentrations of ADP. ADP may be able to induce slight affinity changes in the integrin receptor that allows some fibrinogen binding; however, in the absence of CalDAG-GEFI effects, the receptor cannot complete the conformational change that results in the change in the conformation of bound fibrinogen. This interpretation is consistent with the failure of activated thrombopathic platelets to interact with bead immobilized fibrinogen (J. L. Catalfamo et al., Blood 67:1568-1577 (1986)). Changes in ligand conformation likely play a key role in outside-in signaling events through the alphaIIb-beta3 integrin that lead to complete affinity and avidity modulation necessary for full platelet aggregation and eventual clot retraction. The relationship between dysfunctional CalDAG-GEFI and impaired cAMP metabolism identified in platelets obtained from thrombopathic Basset hounds is interesting. It is possible that platelet Rap1b or other CalDAG-GEFI-activated signaling molecules have roles not previously recognized in pathways that regulate PDE activity and cAMP levels. It is also possible that CalDAG-GEFI serves a scaffolding function or acts as a binding partner for PDE and other signal transduction molecules in addition to its function as a GEF for Rap1b. This type of relationship has been documented in other cell types, including cardiac myocytes in which muscle A kinase-anchoring protein acts as a scaffolding protein for PDE4D3, protein kinase A, and Epac1, a guanine nucleotide exchange factor activated by cAMP (K. L. Dodge-Kafka and M. S. Kapiloff, European J Cell Biol 85:593-602 (2006)). It would be informative to evaluate cAMP metabolism in CalDAG-GEFI knockout mice.

Three distinct mutations were identified in the gene encoding CalDAG-GEFI. These mutations were all located within regions of the gene encoding structurally conserved regions within the catalytic domain of the protein. As a result of these mutations, affected dogs experienced a profound degree of platelet dysfunction and abnormal bleeding tendencies. The similarity of the platelet dysfunction observed in affected dogs to those of knockout mouse was striking. The finding of mutations in 3 different dog breeds with platelet dysfunction suggests that functional mutations in the CalDAG-GEFI gene may be associated with similar defects in human patients. This finding is underscored by the realization that most human patients with congenital platelet disorders have primary secretion defects of unknown etiology (A. K. Rao and J. Gabbeta, Arterioscler Thromb Vasc Biol 20:285-289 (2000)). CalDAG-GEFI has been demonstrated to play a critical role in mouse and canine function. This protein is involved in signal transduction events that are important for inside-out as well as outside-in integrin signaling events. The protein also may play an important role in regulating the platelet release reaction and likely plays a role in cAMP metabolism and PDE regulation. CalDAG-GEFI may be a new target for drugs designed and developed to regulate platelet function. Future studies will be aimed at evaluating CalDAG-GEFI function in thrombopathic Basset hound platelets. Efforts will also be made to evaluate CalDAG-GEFI expression in thrombopathic Landseer platelets if materials become available.

Example III

Calcium Diacylglycerol Guanine Nucleotide Exchange Factor I (CalDAG-GEF1) Gene Mutations in a Thrombophathic Simmental Calf A. Abstract Simmental thrombopathia is an inherited platelet disorder that closely resembles the platelet disorders described in Basset hounds and Eskimo Spitz dogs. Recently two different mutations in the gene encoding calcium diacylglycerol guanine nucleotide exchange factor I (CalDAG-GEFI) were described to be associated with the Basset hound and Spitz thrombopathia disorders and a third distinct mutation was identified in CalDAG-GEFI in thrombopathic Landseers of European Continental Type. The gene encoding CalDAG-GEFI was sequenced using DNA obtained from normal cattle and from a thrombopathic calf studied in Canada. The affected calf was found to have a nucleotide change (c.701 T>C) which would result in the substitution of a proline for a leucine within structurally conserved region two (SCR2) of the catalytic domain of the protein. This change is likely responsible for the thrombopathic phenotype observed in Simmental cattle and underscores the critical nature of this signal transduction protein in platelets.

B. Introduction, Methods, and Results

An inherited intrinsic platelet disorder was first described in Simmental cattle in 1980 and was subsequently described and studied by several investigators in Canada and in the United States between 1980 and 2000 (Frojmovic M M et al., Thromb Haemostas 76:1047-1052 (1996); Gentry P A et al., Can J Vet Res 61:128-133 (1997); Mapletoft R J et al., Can Vet J 41:791-793 (2000); Navarre C B et al., J Vet Intern Med 9:283-285 (1995); Searcy G P et al., Can J Vet Res 54:394-396, (1990); Searcy G P et al., Thromb Haemostas 71:240-246 (1994); Steficek B A et al., J Vet Diagn Invest 5:202-207 (1993); and Steficek B A et al., Thromb Res 72:145-153 (1993)). Affected cattle experienced mild to severe bleeding episodes including epistaxis, gingival bleeding, and hematuria. Bleeding became severe in situations of trauma or following surgical procedures. The platelet disorder closely resembles the platelet disorders described in Basset hounds and Eskimo Spitz dogs at the biochemical and functional levels (Boudreaux M K et al., J Vet Intern Med 8:93-98, (1994); Catalfamo J L et al., Blood 67:1568-1577 (1986); Johnstone I B et al., Can Vet J. 20:211-215 (1979)). The disorder in both species is characterized by impaired platelet aggregation responses to ADP and collagen and a delayed but full response to thrombin. Thrombopathic platelets release serotonin normally in response to thrombin and support normal clot retraction. Platelet membrane concentrations of glycoproteins IIb and IIIa (integrin alpha IIb-beta 3) are normal as is platelet morphology at the electron microscopic level.

Recently mutations in the gene that encodes calcium diacylglycerol guanine nucleotide exchange factor I (CalDAG-GEFI), were identified and associated with thrombopathias in Basset hounds, Spitz dogs, and Landseers of European Continental Type (ECT) (Boudreaux M K et al., Translational Research 150:81-92 (2007)). All of the mutations were located in areas of the gene encoding for structurally conserved regions (SCRs) of the catalytic domain. CalDAG-GEFI, also known as Ras guanyl releasing protein 2 (RasGRP2), is a critical signal transduction protein that functions as a guanine nucleotide exchange factor (GEF) in platelets leading to the activation of the GTPase Rap1b (Crittenden J R et al., Nature Medicine 10:982-986 (2004)). CalDAG-GEFI contains 4 major domain structures including the Ras exchanger motif (REM), a catalytic domain, two EF hand domains for interaction with calcium, and a C1 domain for interaction with diacylglycerol (DAG) and phorbol esters (Eto K et al., Proc Natl Acad Sci 99:12819-12824 (2002.)). The catalytic domain of CalDAG-GEFI contains five structurally conserved regions (SCRs) that are critically important for interaction of the GEF with Rap1b. The SCRs within CalDAG-GEFI are not only conserved across species lines but are also highly conserved across multiple types of GEFs in different cell types, thus emphasizing the importance of maintaining a particular structure for proper function. Guanine nucleotide exchange factors facilitate the exchange of GTP for GDP in their target GTPases. GTP-bound GTPases in turn become activated and engage their effector proteins (Boriack-Sjodin P A et al., Nature 394:337-343 (1998)). Rap1b is present in high concentrations in platelets and is thought to modulate the affinity and avidity of integrin alphaIIb-beta 3 leading to fibrinogen binding and platelet aggregation (Bertoni A. et al., J Biol. Chem. 277:25715-25721 (2002)). Most of the platelet agonists that ultimately activate Rap1b do so either directly or indirectly through stimulation of $G_i$-coupled receptors leading to inhibition of adenylate cyclase, lowering of cAMP, and generation of second messengers including calcium and DAG. Calcium and DAG bind to the EF hand and C1 domains of CalDAG-GEFI resulting in activation of the GEF which then mediates the activation of Rap1b. The cycle is completed when GTPase-activating proteins (GAPs) catalyze the conversion of Rap1 b-GTP to inactive Rap1 b-GDP forms.

The platelet disorders described in dogs and CalDAG-GEFI knock-out mice are strikingly similar to the platelet disorder described in Simmental cattle. The purpose of this study was to evaluate the gene encoding CalDAG-GEFI in a thrombopathic Simmental calf and compare the DNA sequence obtained to DNA sequences obtained in its full siblings, as well as other cattle without a bleeding diathesis due to thrombopathia. Particular attention would be paid to areas of the gene encoding for SCRs of the catalytic domain.

Genomic DNA was harvested from EDTA-anticoagulated blood obtained from normal cattle using the QIAamp DNA Blood Mini Kit (Qiagen, Inc., Valencia, Calif.). Primers were designed within introns flanking coding regions of the gene to assure assessment of all exon-intron splice sites. Primers were designed using sequence obtained from the bovine genome available on GenBank. The correct area of the bovine genome was located by comparing human CalDAG-GEFI cDNA sequence available on GenBank (gi:24797102). The coding region sequence information obtained in this study for bovine CalDAG-GEFI was submitted to GenBank (Accession #EF633475). DNA was isolated from blood obtained from 20 cattle of varying breeds, 18 Simmental cattle, and two Simmental-crosses not related to the thrombopathic calf. The Simmental-cross cattle included one calf with von Willebrand's disease (diagnosis was based on the presence of a bleeding diathesis combined with normal coagulation screening assays, normal platelet numbers, and a von Willebrand factor antigen concentration=8%; analysis performed by the Animal Health Diagnostic Center, College of Veterinary Medicine, Cornell University) and the dam of that calf. DNA samples from three Simmental cattle that were related to a thrombopathic calf studied at Michigan State University during the 1990's, a thrombopathic calf (#145) studied by Mapletoft, et al (Mapletoft R J et al., Can Vet J 41:791-793 (2000)) at the University of Saskatchewan, 22 of its embryo transfer (ET) full-siblings, and 1 ET half-sibling, as well as 10 cows related to the affected embryo donor were also evaluated. The gene sequence encoding Rap1b was also evaluated in the thrombopathic calf to rule out the possibility of a mutation in the target protein of CalDAG-GEFI. The coding region of Rap1b was found to be identical to cow genome sequence available on GenBank (data not shown).

Polymorphisms were found within several of the intronic sequences of the gene encoding CalDAG-GEFI. Most of the intronic polymorphisms constituted single nucleotide changes and were not considered to be of significance since they were found in the affected calf as well as within normal cattle. A 177-base-pair deletion in the intron between exons 3 and 4 was noted in both normal cows and in the thrombopathic calf when sequences were compared to the bovine genome. An 18-base-pair deletion in the intron between exons 12 and 13 was noted in the DNA of some normal cattle but was not present in the thrombopathic calf. Within exon 4 of the coding region a single nucleotide change was noted in both affected and normal cattle (c.281A>C) compared to the bovine genome sequence. This change (CAT to CCT) would result in the substitution of a proline for a histidine. When dog, equine, and human sequences were compared to bovine sequence for this region it was noted that dog, human, and equine sequences encoded for a proline in this location; thus this may constitute either a variant or an error in the bovine sequence entered on GenBank.

Two single nucleotide changes which altered amino acids were documented within the coding region of the CalDAG-GEFI gene in the affected calf in a homozygous state. One change was documented within exon 6 (c.653C>T) which would be predicted to result in the substitution of a leucine for a proline (CCG to CTG). Although seemingly significant, this homozygous change was also documented in one related Canadian cow and in the Simmental-cross dam of the calf with von Willebrand's disease. These cows did not have a bleeding diathesis and platelet aggregation studies performed on the obligate carrier dam and calf with vWD were normal (data not shown). This change occurred within an area of the gene encoding for a segment between SCR1 and SCR2. The predicted substitution apparently does not impact significantly on the function of the enzyme. Several other cattle, both Simmentals and non-Simmentals were found to be heterozygous for this mutation.

The other homozygous mutation in the thrombopathic calf was a single nucleotide change in exon 7 (c.701T>C). This change would be predicted to result in the substitution of a proline for a leucine (CTC to CCC). This change was considered highly significant since it was located in a region of the gene encoding for SCR2 (Table 2).

TABLE 2

DNA sequences representing the end of intron 6 and the beginning of exon 7 (underlined) for CalDAG-GEFI in a normal cow and a thrombopathic calf.

Normal Cow    GTCCCCCAGG<u>AATTCCTGCACC</u>  (SEQ ID NO: 41)

Thrombopathic GTCCCCCAGG<u>AACCCCTGCACC</u>  (SEQ ID NO: 42)
calf

The single nucleotide change is shown in bold.
The codon change of CTC to CCC would be predicted to result in the substitution of a proline for a leucine within structurally conserved region two (SCR2) of CalDAG-GEFI.

Proline is highly conserved in this segment of the catalytic domain across species lines and a change at this location would likely impact on the function of the protein. This change was not documented in the DNA samples of any of the non-related cattle (Simmentals or non-Simmentals) or in the DNA samples of three clinically normal Simmental cattle related to the affected calf studied at Michigan State. However, 17 of the 23 siblings of the thrombopathic Canadian calf and 6 of the related cows were found to be heterozygous for this mutation. As expected, none of these siblings or cows had a bleeding diathesis since this disorder is inherited as an autosomal recessive condition. Although this nucleotide change is considered highly significant in this location of the gene, evaluation of DNA obtained from other affected calves will be necessary to completely confirm the significance of this mutation.

CalDAG-GEFI is critically important in mediating the effects of agonists, such as ADP and collagen, that signal either directly or indirectly through $G_i$. The ability of thrombin to activate thrombopathic platelets and induce clot retraction implies that at least one of the thrombin receptors is able to by-pass CalDAG-GEFI and activate Rap1b directly or mediate activation via a Rap1b-independent pathway. Human platelets have at least two thrombin receptors, protease activated receptor 1 (PAR1) and protease activated receptor 4 (PAR4). PAR1 and PAR4 signaling are biphasic with PAR1 activation resulting in a rapid spike in calcium influx followed by a slower and more prolonged calcium influx mediated by PAR4 (Covic L et al., Biochem 39:5458-5467 (2000.)). PAR4 generates a more sustained calcium signal and is considered to be more effective than PAR1 in generating secondary signals necessary for complete platelet activation. Based on platelet cDNA sequence findings, it is likely that canine platelets are similar to human platelets with regard to platelet PAR receptors. Conceivably, the delayed thrombin response observed in thrombopathic canine platelets is mediated via PAR4 which may not require CalDAG-GEFI in the signaling pathway leading to activation of Rap1b. PAR receptor types have not been determined for bovine platelets; however, based on similar impaired platelet function phenotypes in thrombopathic cattle it is likely that bovine platelets also possess PAR1 and PAR4 thrombin receptors.

This is the second species with a documented inherited intrinsic platelet disorder related to impaired signal transduction and inability to change the affinity/avidity of the alphaIIb-beta 3 receptor to be identified with a spontaneous mutation in the gene encoding CalDAG-GEFI. Thus far all of the spontaneous mutations have been detected within areas of the gene encoding structurally conserved regions of the catalytic domain of the GEF (Table 3).

TABLE 3

Amino acid sequences of the structurally conserved regions (SCRs)
within the catalytic unit of CalDAG-GEFI.

| | | |
|---|---|---|
| SCR1 = | FDHLEPLELAEHLTYLEYRSFCKI | (SEQ ID NO: 26) |
| SCR2 = | RAGVITHFVHVAEELLHLQNFNTLMAVVGGLSHSSISRLKETH | (SEQ ID NO: 27) |
| SCR3 = | GFRFPILGVHLKDLVALQLALPD | (SEQ ID NO: 28) |
| SCR4 = | RLNGAK | (SEQ ID NO: 29) |
| SCR5 = | LYQLSLQREPR | (SEQ ID NO: 30) |

Simmental Cattle with Thrombopathia have substitution of a C for a T at position 701 (c.701 T>C) in Exon 7 (CTC to CCC) resulting in the change of a leucine to a proline at amino acid position 234. This is located in SCR2. Basset hounds with Thrombopathia are missing the F (amino acid 170) in SCR1. This is due to a deletion in nucleotides 509, 510, and 511 (c.509_511delTCT). Eskimo Spitz with Thrombopathia have a single nucleotide duplication between nucleotides 452 and 453 (c.452dupA) resulting in a frame shift starting at the codon encoding D (amino acid 151) near the beginning of SCR1. Landseers-ECT with Thrombopathia have a premature stop codon at the codon encoding R (amino acid 328) due to a substitution of a T for a C (CGA to TGA) at nucleotide 982 (c.982C>T) at the beginning of the sequence encoding SCR4.

The phenotype of cattle and dogs with these mutations are strikingly similar to each other and to the phenotype observed in CalDAG-GEFI knockouts. Signal transduction platelet disorders are the most commonly observed inherited intrinsic platelet disorders in people and in most cases the cause is unknown (Rao and Gabbeta, Arterioscler Thromb Vasc Biol 20:285-289 (2000)). It is likely that mutations in the CalDAG-GEFI gene result in similar platelet disorders in people.

Platelets from a thrombopathic calf were not available for this study negating the ability to perform further specific biochemical studies. Western blots and functional studies, including Rap1 activation pull-down assays, would be useful in determining the effects of this mutation on CalDAG-GEFI at the quantitative and qualitative level.

This disorder in the homozygous state is considered to be rare at the present time. However, the identification of this mutation provides a means to test potential carriers and eliminate this disease from breeding animals.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the present invention.

I claim:

1. A method for identifying a Basset hound as a carrier of a deletion mutation from nucleotide 509 to nucleotide 511 of SEQ ID NO:2, which deletion mutation is associated with thrombopathy, the method comprising:
   (a) analyzing all or part of a nucleic acid sequence in a biological sample from the Basset hound to determine whether the Basset hound has the deletion mutation from nucleotide 509 to nucleotide 511 of SEQ ID NO:2; and
   (b) identifying the Basset hound as a carrier of the deletion mutation from nucleotide 509 to nucleotide 511 of SEQ ID NO:2 if the deletion mutation is present.

2. The method of claim 1, wherein the nucleic acid sequence analyzed is genomic DNA, cDNA, or mRNA.

3. The method of claim 1, wherein analyzing comprises performing hybridization using at least one oligonucleotide that specifically hybridizes to a CalDAG-GEF1 gene comprising the mutation.

4. The method of claim 3, wherein the oligonucleotide does not hybridize to a wild-type CalDAG-GEF1 gene.

5. The method of claim 3, wherein the oligonucleotide comprises a nucleotide sequence selected from the group consisting of SEQ ID NOs:8-11.

6. The method of claim 1, wherein analyzing comprises sequencing or performing nucleic acid amplification.

7. A method for identifying an Eskimo Spitz as a carrier of an insertion mutation of A between nucleotides 452 and 453 of SEQ ID NO:2, which insertion mutation is associated with thrombopathy, the method comprising:
   (a) analyzing all or part of a nucleic acid sequence in a biological sample from the Eskimo Spitz to determine whether the Eskimo Spitz has the insertion mutation of A between nucleotides 452 and 453 of SEQ ID NO:2; and
   (b) identifying the Eskimo Spitz as a carrier of the insertion mutation of A between nucleotides 452 and 453 of SEQ ID NO:2 if the insertion mutation is present.

8. The method of claim 7, wherein the nucleic acid sequence analyzed is genomic DNA, cDNA, or mRNA.

9. The method of claim 7, wherein analyzing comprises performing hybridization using at least one oligonucleotide that specifically hybridizes to a CalDAG-GEF1 gene comprising the mutation.

10. The method of claim 9, wherein the oligonucleotide does not hybridize to a wild-type CalDAG-GEF1 gene.

11. The method of claim 9, wherein the oligonucleotide comprises a nucleotide sequence selected from the group consisting of SEQ ID NO:12 or SEQ ID NO:13.

12. The method of claim 7, wherein analyzing comprises sequencing or performing nucleic acid amplification.

13. A method for identifying a Landseer as a carrier of a substitution mutation of T for C at nucleotide position 982 of SEQ ID NO:2, which substitution mutation is associated with thrombopathy, the method comprising:
   (a) analyzing all or part of a nucleic acid sequence in a biological sample from the Landseer to determine whether the Landseer has the substitution mutation of T for C at nucleotide position 982 of SEQ ID NO:2; and
   (b) identifying the Landseer as a carrier of the substitution mutation of T for C at nucleotide position 982 of SEQ ID NO:2 if the insertion mutation is present.

14. The method of claim 13, wherein the nucleic acid sequence analyzed is genomic DNA, cDNA, or mRNA.

15. The method of claim 13, wherein analyzing comprises performing hybridization using at least one oligonucleotide that specifically hybridizes to a CalDAG-GEF1 gene comprising the mutation.

16. The method of claim 15, wherein the oligonucleotide does not hybridize to a wild-type CalDAG-GEF1 gene.

17. The method of claim 15, wherein the oligonucleotide comprises a nucleotide sequence selected from the group consisting of SEQ ID NO:14 or SEQ ID NO:15.

18. The method of claim 13, wherein analyzing comprises sequencing or performing nucleic acid amplification.

19. A method for screening for mutations in a canine CalDAG-GEF1 gene comprising SEQ ID NO:2, the method comprising:
   (a) obtaining a nucleic acid sample from the canine;
   (b) analyzing all or part of the nucleic acid sequence of the sample;
   (c) comparing the nucleic acid sequence from the canine to SEQ ID NO:2; and
   (b) identifying any differences in sequences between SEQ ID NO:2 and the canine nucleic acid as mutations in the CalDAG-GEF1 gene.

* * * * *

SEQUENCE LISTING

```
<160> NUMBER OF SEQ ID NOS: 42

<210> SEQ ID NO 1
<211> LENGTH: 2224
<212> TYPE: DNA
<213> ORGANISM: Canis familiaris

<400> SEQUENCE: 1
cgcatctgca gctaggccgg ggggcgggag agcacagagg tgtcgcggcc tgttcagggt      60
gcgggatccg tgccgcgggt ctcaagaggt ccggcccgag ccccgcggga ggcccagagt     120
gcagcgtgac ctcgcccacc cgcgccggcc gccatggcgg gcgctctgga cctggacaag     180
ggctgcaccg tggaggagct gctccgcggc tgcatcgaag ccttcgatga ctccgggaag     240
gtgcgggacc cgcagctggt gcgcatgttt ctcatgatgc acccttggta catcccttcc     300
tctcagctgg cggcaaagct gctccacatc tatcaacaat cccggaagga taactccaat     360
tcgctgcagg tgaaaacgtg ccacctggtc aggtactgga tctcagcatt cccagcagag     420
tttgacttga accctgagct cgctgagcag atcaaggagc tgaaggctct gctagaccaa     480
gaagggaacc ggcgccacag cagcctcatt gacatcgaga gcgtccccac ctacaagtgg     540
```

-continued

```
aagcggcagg tgacccagcg gaaccctgta gcacagaaaa aacgaaagat gtccctattg      600
ttcgaccacc tggaacccett ggaactagca gagcatctca cctacttaga gtatcgctcc     660
ttctgcaaga tcctgtttca ggactatcac agttttgtga ctcatggctg caccgtggac     720
aaccccgtcc tggagagatt catctccctc ttcaacagtg tctcacagtg ggtgcagctt     780
atgattctca gcaagcccac tgcccctcag cgtgccctgg tcatcacgca ctttgtccac     840
gtggcagaga agctgcttca cttgcagaac ttcaacactc tgatggccgt ggtcggaggc     900
ctgagccaca gctccatctc ccgcctcaag gagactcaca gtcatgttag ctctgagacc     960
attaagctct gggaaggtct gacagaacta gtgacggcca cgagcaacta tggcaactac    1020
cggcgccggc tggcagcctg tgtgggtttc cgctttccta tcctgggtgt acacctcaag    1080
gacctggtgg ctctgcagct ggcactgcct gactggctgg accctgcccg acccgactt     1140 aatggggcca agatgaagca gctcttcagc atcctggagg agctggccat ggtgaccagc    1200
cttcggccac cagtgcaggc caaccctgat ctgctgagcc tactcacggt atctctggat    1260
cagtatcaga cagaggatga actctaccag ctgtccctgc agcgggagcc acgctccaag    1320
tcctcgccaa ccagccccac aagctgcacc ccacctcccc ggcccccagt tctggatgag    1380
tggacctcag ctgccaaacc caagctggac caggcactcc tggtggaaca catcgagaag    1440
atggtggagt ctgtgttccg gaactttgac gtcgatgggg atggccacat ctcacaggaa    1500
gagttccaga tcatccgtgg gaacttccct tacctcagcg cctttgggga cctcgaccag    1560
aaccaggatg ctgcatcag cagggaggag atggtctctt acttcctgcg ctccagctcg     1620
gtgctgggcg gccgcatggg cttcgtgcac aacttccacg agagcagctc cctgcgcccg    1680
gttgcctgcc gccactgcaa ggccctgatc ctgggcatct acaagcaggg cctcaaatgc    1740
cgagcctgcg gtgtgaactg ccacaaacag tgtaaagacc gtctgtcggt tgaatgccgg    1800
cgccgggcac agagtgtgag tctggagggg tctgcaccct caccctcacc cacccatcac    1860
cgggccttca gcttctccct gccccgccca ggtaggcgag gctcccggcc tccagagatc    1920
cgagaagagg aggtgcaagc agtggaggac ggtgtattcg acatccactt gtaatggatg    1980
ttgtgactgg atcaagcact cctatctgcc ttggagaaaa gacttggacc agagcaggaa    2040
gcctggggtg ctggggcagc aggctggggc tggggggtgg ggtgtgaggg tggcatgcag    2100
ctggaggttg ggccagggct ggcgtcccta aggttgtaca gactcttgtg aatatttgta    2160
ttttccagat ggaataaaaa ggcccgtgta atttttccag atggaataaa aaggcccgtg    2220
taat                                                                  2224
```

<210> SEQ ID NO 2
<211> LENGTH: 1821
<212> TYPE: DNA
<213> ORGANISM: Canis familiaris

<400> SEQUENCE: 2

```
atggcgggcg ctctggacct ggacaagggc tgcaccgtgg aggagctgct ccgcggctgc      60
atcgaagcct tcgatgactc cgggaaggtg cgggacccgc agctggtgcg catgtttctc     120
atgatgcacc cttggtacat cccttcctct cagctggcgg caaagctgct ccacatctat     180
caacaatccc ggaaggataa ctccaattcg ctgcaggtga aaacgtgcca cctggtcagg     240
tactggatct cagcattccc agcagagttt gacttgaacc ctgagctcgc tgagcagatc     300
aaggagctga aggctctgct agaccaagaa gggaaccggc gccacagcag cctcattgac     360
atcgagagcg tccccaccta caagtggaag cggcaggtga cccagcggaa ccctgtagca     420
```

```
cagaaaaaac gaaagatgtc cctattgttc gaccacctgg aacccttgga actagcagag    480
catctcacct acttagagta tcgctccttc tgcaagatcc tgtttcagga ctatcacagt    540
tttgtgactc atggctgcac cgtggacaac cccgtcctgg agagattcat ctccctcttc    600
aacagtgtct cacagtgggt gcagcttatg attctcagca agcccactgc ccctcagcgt    660
gccctggtca tcacgcactt tgtccacgtg cagagaagc tgcttcactt gcagaacttc    720
aacactctga tggccgtggt cggaggcctg agccacagct ccatctcccg cctcaaggag    780
actcacagtc atgttagctc tgagaccatt aagctctggg aaggtctgac agaactagtg    840
acggccacga gcaactatgg caactaccgg cgccggctgg cagcctgtgt gggtttccgc    900
tttcctatcc tgggtgtaca cctcaaggac ctggtggctc tgcagctggc actgcctgac    960
tggctggacc ctgcccggac ccgacttaat ggggccaaga tgaagcagct cttcagcatc   1020
ctggaggagc tggccatggt gaccagcctt cggccaccag tgcaggccaa ccctgatctg   1080
ctgagcctac tcacggtatc tctggatcag tatcagacag aggatgaact ctaccagctg   1140
tccctgcagc gggagccacg ctccaagtcc tcgccaacca gccccacaag ctgcacccca   1200
cctccccggc ccccagttct ggatgagtgg acctcagctg ccaaacccaa gctggaccag   1260
gcactcctgg tggaacacat cgagaagatg gtggagtctg tgttccggaa cttggacgtc   1320
gatggggatg ccacatctc acaggaagag ttccagatca tccgtgggaa cttcccttac   1380
ctcagcgcct ttggggacct cgaccagaac caggatggct gcatcagcag ggaggagatg   1440
gtctcttact tcctgcgctc cagctcggtg ctgggcggcc gcatgggctt cgtgcacaac   1500
ttccacgaga gcagctccct gcgcccggtt gcctgccgcc actgcaaggc cctgatcctg   1560
ggcatctaca gcagggcct caaatgccga gcctgcggtg tgaactgcca caacagtgt   1620 aaagaccgtc tgtcggttga atgccggcgc cgggcacaga gtgtgagtct ggaggggtct   1680
gcaccctcac cctcacccac ccatcaccgg gccttcagct tctccctgcc ccgcccaggt   1740
aggcgaggct cccggcctcc agagatccga aagaggagg tgcaagcagt ggaggacggt   1800
gtattcgaca tccacttgta a                                              1821

<210> SEQ ID NO 3
<211> LENGTH: 1818
<212> TYPE: DNA
<213> ORGANISM: Canis familiaris

<400> SEQUENCE: 3
atggcgggcg ctctggacct ggacaagggc tgcaccgtgg aggagctgct ccgcggctgc     60
atcgaagcct cgatgactc cgggaaggtg cgggaccccgc agctggtgcg catgtttctc    120
atgatgcacc cttggtacat cccttcctct cagctggcgg caaagctgct ccacatctat    180
caacaatccc ggaaggataa ctccaattcg ctgcaggtga aaacgtgcca cctggtcagg    240
tactggatct cagcattccc agcagagttt gacttgaacc ctgagctcgc tgagcagatc    300
aaggagctga aggctctgct agaccaagaa gggaaccggc gccacagcag cctcattgac    360
atcgagagcg tccccaccta caagtggaag cggcaggtga cccagcggaa ccctgtagca    420
cagaaaaaac gaaagatgtc cctattgttc gaccacctgg aacccttgga actagcagag    480
catctcacct acttagagta tcgctccctgc aagatcctgt ttcaggacta tcacagtttt    540
gtgactcatg gctgcaccgt ggacaacccc gtcctggaga gattcatctc cctcttcaac    600
agtgtctcac agtgggtgca gcttatgatt ctcagcaagc ccactgcccc tcagcgtgcc    660
```

-continued

```
ctggtcatca cgcactttgt ccacgtggca gagaagctgc ttcacttgca gaacttcaac      720
actctgatgg ccgtggtcgg aggcctgagc cacagctcca tctcccgcct caaggagact      780
cacagtcatg ttagctctga gaccattaag ctctgggaag gtctgacaga actagtgacg      840
gccacgagca actatggcaa ctaccggcgc cggctggcag cctgtgtggg tttccgcttt      900
cctatcctgg gtgtacacct caaggacctg gtggctctgc agctggcact gcctgactgg      960
ctggaccctg cccggacccg acttaatggg gccaagatga agcagctctt cagcatcctg     1020
gaggagctgg ccatggtgac cagccttcgg ccaccagtgc aggccaaccc tgatctgctg     1080
agcctactca cggtatctct ggatcagtat cagacagagg atgaactcta ccagctgtcc     1140
ctgcagcggg agccacgctc caagtcctcg ccaaccagcc ccacaagctg cacccccacct    1200 cccccggcccc cagttctgga tgagtggacc tcagctgcca aacccaagct ggaccaggca    1260
ctcctggtgg aacacatcga aagatggtg gagtctgtgt tccggaactt tgacgtcgat      1320
ggggatggcc acatctcaca ggaagagttc agatcatcc gtgggaactt cccttacctc      1380
agcgcctttg gggacctcga ccagaaccag gatggctgca tcagcaggga ggagatggtc     1440
tcttacttcc tgcgctccag ctcggtgctg ggcggccgca tgggcttcgt gcacaacttc     1500
cacgagagca gctccctgcg cccggttgcc tgccgccact gcaaggccct gatcctgggc     1560
atctacaagc agggcctcaa atgccgagcc tgcggtgtga actgccacaa acagtgtaaa     1620
gaccgtctgt cggttgaatg ccggcgccgg gcacagagtg tgagtctgga ggggtctgca     1680
ccctcaccct cacccaccca tcaccggggcc ttcagcttct ccctgcccccg cccaggtagg    1740 cgaggctccc ggcctccaga gatccgagaa gaggaggtgc aagcagtgga ggacggtgta    1800
ttcgacatcc acttgtaa                                                    1818
```

<210> SEQ ID NO 4
<211> LENGTH: 1822
<212> TYPE: DNA
<213> ORGANISM: Canis familiaris

<400> SEQUENCE: 4

```
atggcgggcg ctctggacct ggacaagggc tgcaccgtgg aggagctgct ccgcggctgc       60
atcgaagcct tcgatgactc cgggaaggtg cgggacccgc agctggtgcg catgtttctc     120
atgatgcacc cttggtacat cccttcctct cagctggcgg caaagctgct ccacatctat     180
caacaatccc ggaaggataa ctccaattcg ctgcaggtga aaacgtgcca cctggtcagg     240
tactggatct cagcattccc agcagagttt gacttgaacc ctgagctcgc tgagcagatc     300
aaggagctga aggctctgct agaccaagaa gggaaccggc ccacagcag cctcattgac     360 atcgagagcg tccccaccta caagtggaag cggcaggtga cccagcggaa ccctgtagca     420
cagaaaaaac gaaagatgtc cctattgttc gaaccacctg gaacccttgg aactagcaga     480
gcatctcacc tacttagagt atcgctcctt ctgcaagatc ctgtttcagg actatcacag     540
ttttgtgact catggctgca ccgtggacaa ccccgtcctg gagagattca tctccctctt      600
caacagtgtc tcacagtggg tgcagcttat gattctcagc aagcccactg cccctcagcg     660
tgccctggtc atcacgcact ttgtccacgt ggcagagaag ctgcttcact tgcagaactt     720
caacactctg atggccgtgg tcggaggcct gagccacagc tccatctccc gcctcaagga     780
gactcacagt catgttagct ctgagaccat taagctctgg gaaggtctga cagaactagt     840
gacggccacg agcaactatg gcaactaccg gcgccggctg gcagcctgtg tgggtttccg     900
ctttcctatc ctgggtgtac acctcaagga cctggtggct ctgcagctgg cactgcctga    960
```

-continued

```
ctggctggac cctgcccgga cccgacttaa tggggccaag atgaagcagc tcttcagcat   1020
cctggaggag ctggccatgg tgaccagcct tcggccacca gtgcaggcca accctgatct   1080
gctgagccta ctcacggtat ctctggatca gtatcagaca gaggatgaac tctaccagct   1140
gtccctgcag cgggagccac gctccaagtc ctcgccaacc agccccacaa gctgcacccc   1200
acctccccgg cccccagttc tggatgagtg gacctcagct gccaaaccca gctggacca   1260 ggcactcctg gtgaacaca tcgagaagat ggtggagtct gtgttccgga actttgacgt   1320
cgatggggat ggccacatct cacaggaaga gttccagatc atccgtggga acttcccta   1380 cctcagcgcc tttggggacc tcgaccagaa ccaggatggc tgcatcagca gggaggagat   1440
ggtctcttac ttcctgcgct ccagctcggt gctgggcggc cgcatgggct tcgtgcacaa   1500
cttccacgag agcagctccc tgcgcccggt tgcctgccgc cactgcaagg ccctgatcct   1560
gggcatctac aagcagggcc tcaaatgccg agcctgcggt gtgaactgcc acaaacagtg   1620
taaagaccgt ctgtcggttg aatgccggcg ccgggcacag agtgtgagtc tggaggggtc   1680
tgcaccctca ccctcaccca cccatcaccg ggccttcagc ttctccctgc ccgcccagg   1740 taggcgaggc tcccggcctc cagagatccg agaagaggag gtgcaagcag tggaggacgg   1800
tgtattcgac atccacttgt aa                                            1822
```

<210> SEQ ID NO 5
<211> LENGTH: 1821
<212> TYPE: DNA
<213> ORGANISM: Canis familiaris
<400> SEQUENCE: 5

```
atggcgggcg ctctggacct ggacaagggc tgcaccgtgg aggagctgct ccgcggctgc    60
atcgaagcct tcgatgactc cgggaaggtg cgggaccgc agctggtgcg catgtttctc   120
atgatgcacc cttggtacat cccttcctct cagctggcgg caaagctgct ccacatctat   180
caacaatccc ggaaggataa ctccaattcg ctgcaggtga aaacgtgcca cctggtcagg   240
tactggatct cagcattccc agcagagttt gacttgaacc ctgagctcgc tgagcagatc   300
aaggagctga aggctctgct agaccaagaa gggaaccggc gccacagcag cctcattgac   360
atcgagagcg tccccaccta caagtggaag cggcaggtga cccagcggaa ccctgtagca   420
cagaaaaaac gaaagatgtc cctattgttc gaccacctgg aacccttgga actagcagag   480
catctcacct acttagagta tcgctccttc tgcaagatcc tgtttcagga ctatcacagt   540
tttgtgactc atggctgcac cgtggacaac cccgtcctgg agagattcat ctccctcttc   600
aacagtgtct cacagtgggt gcagcttatg attctcagca agcccactgc ccctcagcgt   660
gccctggtca tcacgcactt tgtccacgtg gcagagaagc tgcttcactt gcagaacttc   720
aacactctga tggccgtggt cggaggcctg agccacagct ccatctcccg cctcaaggag   780
actcacagtc atgttagctc tgagaccatt aagctctggg aaggtctgac agaactagtg   840
acggccacga gcaactatgg caactaccgg cgccggctgg cagcctgtgt gggttttccgc   900 tttcctatcc tgggtgtaca cctcaaggac ctggtggctc tgcagctggc actgcctgac   960
tggctggacc ctgcccggac ctgacttaat ggggccaaga tgaagcagct cttcagcatc   1020
ctggaggagc tggccatggt gaccagcctt cggccaccag tgcaggccaa ccctgatctg   1080
ctgagcctac tcacggtatc tctggatcag tatcagacag aggatgaact ctaccagctg   1140
tccctgcagc gggagccacg ctccaagtcc tcgccaacca gccccacaag ctgcacccca   1200
```

-continued

```
cctccccggc ccccagttct ggatgagtgg acctcagctg ccaaacccaa gctggaccag    1260
gcactcctgg tggaacacat cgagaagatg gtggagtctg tgttccggaa ctttgacgtc    1320
gatggggatg ccacatctc acaggaagag ttccagatca tccgtgggaa cttcccttac    1380
ctcagcgcct ttggggacct cgaccagaac caggatggct gcatcagcag ggaggagatg    1440
gtctcttact cctgcgctc cagctcggtg ctgggcggcc gcatgggctt cgtgcacaac    1500
ttccacgaga gcagctccct cgcccgggtt gcctgccgcc actgcaaggc cctgatcctg    1560
ggcatctaca gcagggcct caaatgccga gcctgcggtg tgaactgcca caaacagtgt    1620
aaagaccgtc tgtcggttga atgccggcgc cgggcacaga gtgtgagtct ggaggggtct    1680
gcaccctcac cctcacccac ccatcaccgg gccttcagct tctccctgcc ccgcccaggt    1740
aggcgaggct cccggcctcc agagatccga gaagaggagg tgcaagcagt ggaggacggt    1800
gtattcgaca tccacttgta a                                              1821
```

<210> SEQ ID NO 6
<211> LENGTH: 606
<212> TYPE: PRT
<213> ORGANISM: Canis familiaris

<400> SEQUENCE: 6

| Met | Ala | Gly | Ala | Leu | Asp | Leu | Asp | Lys | Gly | Cys | Thr | Val | Glu | Glu | Leu |
|---|---|---|---|---|---|---|---|---|---|---|---|---|---|---|---|
| 1 | | | | 5 | | | | | 10 | | | | | 15 | |

Leu Arg Gly Cys Ile Glu Ala Phe Asp Asp Ser Gly Lys Val Arg Asp
            20                  25                  30

Pro Gln Leu Val Arg Met Phe Leu Met Met His Pro Trp Tyr Ile Pro
        35                  40                  45

Ser Ser Gln Leu Ala Ala Lys Leu Leu His Ile Tyr Gln Gln Ser Arg
    50                  55                  60

Lys Asp Asn Ser Asn Ser Leu Gln Val Lys Thr Cys His Leu Val Arg
65                  70                  75                  80

Tyr Trp Ile Ser Ala Phe Pro Ala Glu Phe Asp Leu Asn Pro Glu Leu
                85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Glu Ser Val Pro Thr Tyr Lys
        115                 120                 125

Trp Lys Arg Gln Val Thr Gln Arg Asn Pro Val Ala Gln Lys Lys Arg
    130                 135                 140

Lys Met Ser Leu Leu Phe Asp His Leu Glu Pro Leu Glu Leu Ala Glu
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Pro Gln Arg Ala Leu Val Ile
    210                 215                 220

Thr His Phe Val His Val Ala Glu Lys Leu Leu His Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Ser Glu Thr Ile Lys Leu

```
                260                 265                 270
Trp Glu Gly Leu Thr Glu Leu Val Thr Ala Thr Ser Asn Tyr Gly Asn
            275                 280                 285

Tyr Arg Arg Arg Leu Ala Ala Cys Val Gly Phe Arg Phe Pro Ile Leu
        290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Thr Val Ser Leu
        355                 360                 365

Asp Gln Tyr Gln Thr Glu Asp Glu Leu Tyr Gln Leu Ser Leu Gln Arg
370                 375                 380

Glu Pro Arg Ser Lys Ser Ser Pro Thr Ser Pro Thr Ser Cys Thr Pro
385                 390                 395                 400

Pro Pro Arg Pro Pro Val Leu Asp Glu Trp Thr Ser Ala Ala Lys Pro
                405                 410                 415

Lys Leu Asp Gln Ala Leu Leu Val Glu His Ile Glu Lys Met Val Glu
            420                 425                 430

Ser Val Phe Arg Asn Phe Asp Val Asp Gly Asp Gly His Ile Ser Gln
        435                 440                 445

Glu Glu Phe Gln Ile Ile Arg Gly Asn Phe Pro Tyr Leu Ser Ala Phe
    450                 455                 460

Gly Asp Leu Asp Gln Asn Gln Asp Gly Cys Ile Ser Arg Glu Glu Met
465                 470                 475                 480

Val Ser Tyr Phe Leu Arg Ser Ser Val Leu Gly Arg Met Gly
                485                 490                 495

Phe Val His Asn Phe His Glu Ser Ser Leu Arg Pro Val Ala Cys
            500                 505                 510

Arg His Cys Lys Ala Leu Ile Leu Gly Ile Tyr Lys Gln Gly Leu Lys
        515                 520                 525

Cys Arg Ala Cys Gly Val Asn Cys His Lys Gln Cys Lys Asp Arg Leu
    530                 535                 540

Ser Val Glu Cys Arg Arg Ala Gln Ser Val Ser Leu Glu Gly Ser
545                 550                 555                 560

Ala Pro Ser Pro Ser Pro Thr His His Arg Ala Phe Ser Phe Ser Leu
                565                 570                 575

Pro Arg Pro Gly Arg Arg Gly Ser Arg Pro Glu Ile Arg Glu Glu
            580                 585                 590

Glu Val Gln Ala Val Glu Asp Gly Val Phe Asp Ile His Leu
        595                 600                 605

<210> SEQ ID NO 7
<211> LENGTH: 115
<212> TYPE: PRT
<213> ORGANISM: Canis familiaris

<400> SEQUENCE: 7

Glu Pro Pro Gly Thr Leu Gly Thr Ser Arg Ala Ser His Leu Leu Arg
1               5                   10                  15

Val Ser Leu Leu Leu Gln Asp Pro Val Ser Gly Leu Ser Gln Phe Cys
            20                  25                  30
```

-continued

```
Asp Ser Trp Leu His Arg Gly Gln Pro Arg Pro Gly Glu Ile His Leu
        35                  40                  45

Pro Leu Gln Gln Cys Leu Thr Val Gly Ala Ala Tyr Asp Ser Gln Gln
    50                  55                  60

Ala His Cys Pro Ser Ala Cys Pro Gly His His Ala Leu Cys Pro Arg
65                  70                  75                  80

Gly Arg Glu Ala Ala Ser Leu Ala Glu Leu Gln His Ser Asp Gly Arg
                85                  90                  95

Gly Arg Arg Pro Glu Pro Gln Leu His Leu Pro Pro Gln Gly Asp Ser
            100                 105                 110

Gln Ser Cys
        115

<210> SEQ ID NO 8
<211> LENGTH: 10
<212> TYPE: DNA
<213> ORGANISM: Canis familiaris

<400> SEQUENCE: 8
atcgctcctg                                                                  10

<210> SEQ ID NO 9
<211> LENGTH: 10
<212> TYPE: DNA
<213> ORGANISM: Canis familiaris

<400> SEQUENCE: 9
ggatcttgca                                                                  10

<210> SEQ ID NO 10
<211> LENGTH: 10
<212> TYPE: DNA
<213> ORGANISM: Canis familiaris

<400> SEQUENCE: 10
ctcctgcaag                                                                  10

<210> SEQ ID NO 11
<211> LENGTH: 10
<212> TYPE: DNA
<213> ORGANISM: Canis familiaris

<400> SEQUENCE: 11
cttgcaggag                                                                  10

<210> SEQ ID NO 12
<211> LENGTH: 10
<212> TYPE: DNA
<213> ORGANISM: Canis familiaris

<400> SEQUENCE: 12
attgttcgaa                                                                  10

<210> SEQ ID NO 13
<211> LENGTH: 10
<212> TYPE: DNA
<213> ORGANISM: Canis familiaris

<400> SEQUENCE: 13
tccaggtggt                                                                  10
```

```
<210> SEQ ID NO 14
<211> LENGTH: 10
<212> TYPE: DNA
<213> ORGANISM: Canis familiaris

<400> SEQUENCE: 14
gcccggacct                                                                10

<210> SEQ ID NO 15
<211> LENGTH: 10
<212> TYPE: DNA
<213> ORGANISM: Canis familiaris

<400> SEQUENCE: 15
cattaagtca                                                                10

<210> SEQ ID NO 16
<211> LENGTH: 1827
<212> TYPE: DNA
<213> ORGANISM: Bos taurus

<400> SEQUENCE: 16
atggcgggca ccctggacct ggacaagggc tgcacggtgg aggagctgct ccgtggttgc        60
atcgaagcct ttgatgattc cgggaaggtg cgggacccgc agctggtgcg catgttcctt       120
atgatgcacc cctggtacat cccttcctct cagctggcgg ccaaactgct ccacatctac       180
caacaatccc ggaaggacaa ctccagctca ctgcaggtga aaacatgcca cctggtcagg       240
tactggatct cagcattccc agcggagttt gacttgaatc ctgagcttgc tgagcagatc       300
aaggagctga aggctctgct agatcaagaa gggaatcgcc ggcacagcag cctcatcgac       360
attgagaacg tccccaccta caagtggaag cggcaggtga cccagcggaa ccccgtggaa       420
cagaagaagc gcaagatgtc cctgctgttt gaccacctgg agcccttgga gctggcggca       480
catctcacct acttggaata tcgctccttc tgcaagatcc tgttccagga ctatcacagt       540
tttgtgactc acggctgcac ggtggacaat cccgtcctgg agcgattcat ctccctcttc       600
aacagtgtct cacagtgggt gcagctgatg attctcagca agcccacagc cccgcagcgg       660 gcggggggtca tcacacactt cgtccacgtg gcagaggaac tcctgcacct gcagaatttc       720
aacacgctga tggcagtggt tgggggcctg agccacagct ccatctcccg cctcaaggag       780
acccacagcc acgtgagccc ggagaccatc aagctctggg aaggtctgac agagctggtg       840
acggccaccg gcaactatgg caactaccgg cgccggctgg cggcctgcgt gggtttccgc       900
ttccccatcc tgggtgttca cctcaaggac ctggtggccc tgcagctggc gctgccggat       960
tggctggacc ccgcccggac ccgactcaat ggggccaaga tgaagcagct cttcagtatc      1020
ctggaggagc tggccatggt gaccagcctc cggcccccgg tgcaagccaa ccctgacctg      1080
ctgagcctgc tgatggtgtc tttggatcaa tatcagacag aggatgagct ctaccagctg      1140
tccctgcagc gggaaccgcg ttctaagtcc tcgccaacca gccccaccac ctgcacaccg      1200
cctccccggc cccggtgctg gaggagtggg acctcggctg ccaaacccaa gctggatcag      1260
gcgatcatgg tggagcacat tgagaagatg gtggagtctg tgttccggaa ctttgacgtc      1320 gatgggacg ccacatctc acaggaggag ttccagatca tccgtgggaa ttttccttat      1380
ctcagcgcct ttgggaccct cgaccagaac caggacggct gcatcagcaa ggaggagatg      1440
gtctcctact ttctgcgctc cagctctatg ctgggcggcc gcatgggctt cgtacacaac      1500
ttccacgaga gcaactcctt gcgcccggtc gcctgccgcc actgcaaggc cctgatcctg      1560
```

| | |
|---|---:|
| ggcatctaca aacagggtct caaatgccga gcctgtggtg tgaactgcca caagcagtgc | 1620 |
| aaggatcgcc tgtcagttga gtgccggcgc cgggcccaga gtatgagtct ggagggggtct | 1680 |
| gcaccctctc cctcgcccac acatacccac catcgcgcct tcagcttctc cctgccccgc | 1740 |
| cctggcagac gaggctcccg gcctccagag atccgagagg aggaggttca dacggtggag | 1800 |
| gacggcgtgt ttgacatcca cttgtaa | 1827 |

<210> SEQ ID NO 17
<211> LENGTH: 1827
<212> TYPE: DNA
<213> ORGANISM: Bos taurus

<400> SEQUENCE: 17

| | |
|---|---:|
| atggcgggca ccctggacct ggacaagggc tgcacggtgg aggagctgct ccgtggttgc | 60 |
| atcgaagcct ttgatgattc cgggaaggtg cgggacccgc agctggtgcg catgttcctt | 120 |
| atgatgcacc cctggtacat cccttcctct cagctggcgg ccaaactgct ccacatctac | 180 |
| caacaatccc ggaaggacaa ctccagctca ctgcaggtga aacatgcca cctggtcagg | 240 |
| tactggatct cagcattccc agcggagttt gacttgaatc ctgagcttgc tgagcagatc | 300 |
| aaggagctga aggctctgct agatcaagaa gggaatcgcc ggcacagcag cctcatcgac | 360 |
| attgagaacg tccccaccta caagtggaag cggcaggtga cccagcggaa ccccgtggaa | 420 |
| cagaagaagc gcaagatgtc cctgctgttt gaccacctgg agcccttgga gctggcggca | 480 |
| catctcacct acttggaata tcgctccttc tgcaagatcc tgttccagga ctatcacagt | 540 |
| tttgtgactc acggctgcac ggtggacaat cccgtcctgg agcgattcat ctccctcttc | 600 |
| aacagtgtct cacagtgggt gcagctgatg attctcagca agcccacagc cccgcagcgg | 660 |
| gcgggggtca tcacacactt cgtccacgtg cagaggaac ccctgcacct gcagaatttc | 720 |
| aacacgctga tggcagtggt tggggggcctg agccacagct ccatctcccg cctcaaggag | 780 |
| acccacagcc acgtgagccc ggagaccatc aagctctggg aaggtctgac agagctggtg | 840 |
| acggccaccg caactatgg caactaccgg cgccggctgg cggcctgcgt gggttttccgc | 900 |
| ttccccatcc tgggtgttca cctcaaggac ctggtggccc tgcagctggc gctgccggat | 960 |
| tggctggacc ccgcccggac ccgactcaat ggggccaaga tgaagcagct cttcagtatc | 1020 |
| ctggaggagc tggccatggt gaccagcctc cggcccccgg tgcaagccaa ccctgacctg | 1080 |
| ctgagcctgc tgatggtgtc tttggatcaa tatcagacag aggatgagct ctaccagctg | 1140 |
| tccctgcagc gggaaccgcg ttctaagtcc tcgccaacca gccccaccac ctgcacaccg | 1200 |
| cctcccggc cccggtgct ggaggagtgg acctcggctg ccaaacccaa gctggatcag | 1260 |
| gcgatcatgg tggagcacat tgagaagatg gtggagtctg tgttccggaa ctttgacgtc | 1320 |
| gatggggacg ccacatctc acaggaggag ttccagatca tccgtgggaa ttttccttat | 1380 |
| ctcagcgcct ttggggacct cgaccagaac caggacggct gcatcagcaa ggaggagatg | 1440 |
| gtctcctact ttctgcgctc cagctctatg ctgggcggcc gcatgggctt cgtacacaac | 1500 |
| tccacgaga gcaactcctt gcgcccggtc gcctgccgcc actgcaaggc cctgatcctg | 1560 |
| ggcatctaca aacagggtct caaatgccga gcctgtggtg tgaactgcca caagcagtgc | 1620 |
| aaggatcgcc tgtcagttga gtgccggcgc cgggcccaga gtatgagtct ggagggggtct | 1680 |
| gcaccctctc cctcgcccac acatacccac catcgcgcct tcagcttctc cctgccccgc | 1740 |
| cctggcagac gaggctcccg gcctccagag atccgagagg aggaggttca dacggtggag | 1800 |
| gacggcgtgt ttgacatcca cttgtaa | 1827 |

<210> SEQ ID NO 18
<211> LENGTH: 1827
<212> TYPE: DNA
<213> ORGANISM: Bos taurus

<400> SEQUENCE: 18

| | | | | | | |
|---|---|---|---|---|---|---|
| atggcgggca | ccctggacct | ggacaagggc | tgcacggtgg | aggagctgct | ccgtggttgc | 60 |
| atcgaagcct | tgatgattc | cgggaaggtg | cgggacccgc | agctggtgcg | catgttcctt | 120 |
| atgatgcacc | cctggtacat | cccttcctct | cagctggcgg | ccaaactgct | ccacatctac | 180 |
| caacaatccc | ggaaggacaa | ctccagctca | ctgcaggtga | aaacatgcca | cctggtcagg | 240 |
| tactggatct | cagcattccc | agcggagttt | gacttgaatc | ctgagcttgc | tgagcagatc | 300 |
| aaggagctga | aggctctgct | agatcaagaa | gggaatcgcc | ggcacagcag | cctcatcgac | 360 |
| attgagaacg | tccccaccta | caagtggaag | cggcaggtga | cccagcggaa | ccccgtggaa | 420 |
| cagaagaagc | gcaagatgtc | cctgctgttt | gaccacctgg | agcccttgga | gctggcggca | 480 |
| catctcacct | acttggaata | tcgctccttc | tgcaagatcc | tgttccagga | ctatcacagt | 540 |
| tttgtgactc | acggctgcac | ggtggacaat | cccgtcctgg | agcgattcat | ctccctcttc | 600 |
| aacagtgtct | cacagtgggt | gcagctgatg | attctcagca | agcccacagc | cctgcagcgg | 660 |
| gcggggtca | tcacacactt | cgtccacgtg | cagaggaaac | tcctgcacct | gcagaatttc | 720 |
| aacacgctga | tggcagtggt | tggggcctg | agccacagct | ccatctcccg | cctcaaggag | 780 |
| acccacagcc | acgtgagccc | ggagaccatc | aagctctggg | aaggtctgac | agagctggtg | 840 |
| acggccaccg | gcaactatgg | caactaccgg | cgccggctgg | cggcctgcgt | gggtttccgc | 900 |
| ttccccatcc | tgggtgttca | cctcaaggac | ctggtggccc | tgcagctggc | gctgccggat | 960 |
| tggctggacc | ccgcccggac | ccgactcaat | ggggccaaga | tgaagcagct | cttcagtatc | 1020 |
| ctggaggagc | tggccatggt | gaccagcctc | cggcccccgg | tgcaagccaa | ccctgacctg | 1080 |
| ctgagcctgc | tgatggtgtc | tttggatcaa | tatcagacag | aggatgagct | ctaccagctg | 1140 |
| tccctgcagc | gggaaccgcg | ttctaagtcc | tcgccaacca | gccccaccac | ctgcacaccg | 1200 |
| cctcccggc | ccccggtgct | ggaggagtgg | acctcggctg | ccaaacccaa | gctggatcag | 1260 |
| gcgatcatgg | tggagcacat | tgagaagatg | gtggagtctg | tgttccggaa | ctttgacgtc | 1320 |
| gatggggacg | gccacatctc | acaggaggag | ttccagatca | tccgtgggaa | ttttccttat | 1380 |
| ctcagcgcct | tgggggacct | cgaccagaac | caggacggct | gcatcagcaa | ggaggagatg | 1440 |
| gtctcctact | ttctgcgctc | cagctctatg | ctgggcggcc | gcatgggctt | cgtacacaac | 1500 |
| ttccacgaga | gcaactcctt | cgcccggtc | gcctgccgcc | actgcaaggc | cctgatcctg | 1560 |
| ggcatctaca | acagggtct | caaatgccga | gctgtggtg | tgaactgcca | caagcagtgc | 1620 |
| aaggatcgcc | tgtcagttga | gtgccggcgc | cgggcccaga | gtatgagtct | ggagggtct | 1680 |
| gcaccctctc | cctcgcccac | acatacccac | catcgcgcct | tcagcttctc | cctgccccgc | 1740 |
| cctggcagac | gaggctcccg | gcctccagag | atccgagagg | aggaggttca | gacggtggag | 1800 |
| gacggcgtgt | tgacatcca | cttgtaa | | | | 1827 |

<210> SEQ ID NO 19
<211> LENGTH: 1827
<212> TYPE: DNA
<213> ORGANISM: Bos taurus

<400> SEQUENCE: 19

| | | | | | | |
|---|---|---|---|---|---|---|
| atggcgggca | ccctggacct | ggacaagggc | tgcacggtgg | aggagctgct | ccgtggttgc | 60 |

-continued

```
atcgaagcct tgatgattc cgggaaggtg cgggacccgc agctggtgcg catgttcctt        120
atgatgcacc cctggtacat cccttcctct cagctggcgg ccaaactgct ccacatctac        180
caacaatccc ggaaggacaa ctccagctca ctgcaggtga aaacatgcca cctggtcagg        240
tactggatct cagcattccc agcggagttt gacttgaatc ctgagcttgc tgagcagatc        300
aaggagctga aggctctgct agatcaagaa gggaatcgcc ggcacagcag cctcatcgac        360
attgagaacg tccccaccta caagtggaag cggcaggtga cccagcggaa ccccgtggaa        420
cagaagaagc gcaagatgtc cctgctgttt gaccacctgg agcccttgga gctggcggca        480
catctcacct acttggaata tcgctccttc tgcaagatcc tgttccagga ctatcacagt        540
tttgtgactc acggctgcac ggtggacaat cccgtcctgg agcgattcat ctccctcttc        600
aacagtgtct cacagtgggt gcagctgatg attctcagca agcccacagc cctgcagcgg        660 gcggggggtca tcacacactt cgtccacgtg gcagaggaac ccctgcacct gcagaatttc        720
aacacgctga tggcagtggt tggggggcctg agccacagct ccatctcccg cctcaaggag        780
acccacagcc acgtgagccc ggagaccatc aagctctggg aaggtctgac agagctggtg        840
acggccaccg caactatgg caactaccgg cgccggctgg cggcctgcgt gggtttccgc        900 ttcccccatcc tgggtgttca cctcaaggac ctggtggccc tgcagctggc gctgccggat        960
tggctggacc ccgcccggac ccgactcaat ggggccaaga tgaagcagct cttcagtatc       1020
ctggaggagc tggccatggt gaccagcctc cggcccccgg tgcaagccaa ccctgacctg       1080
ctgagcctgc tgatggtgtc tttggatcaa tatcagacag aggatgagct ctaccagctg       1140
tccctgcagc gggaaccgcg ttctaagtcc tcgccaacca gccccaccac ctgcacaccg       1200
cctccccggc cccggtgct ggaggagtgg acctcggctg ccaaacccaa gctggatcag       1260
gcgatcatgg tggagcacat tgagaagatg gtggagtctg tgttccggaa ctttgacgtc       1320 gatgggacg ccacatctc acaggaggag ttccagatca tccgtgggaa ttttccttat       1380
ctcagcgcct tgggggacct cgaccagaac caggacggct gcatcagcaa ggaggagatg       1440
gtctcctact ttctgcgctc cagctctatg ctgggcggcc gcatgggctt cgtacacaac       1500
ttccacgaga gcaactcctt gcgcccggtc gcctgccgcc actgcaaggc cctgatcctg       1560
ggcatctaca acagggtct caaatgccga gcctgtggtg tgaactgcca caagcagtgc       1620
aaggatcgcc tgtcagttga gtgccggcgc cgggcccaga gtatgagtct ggagggggtct       1680 gcaccctctc cctcgcccac acatacccac catcgcgcct tcagcttctc cctgccccgc       1740
cctggcagac gaggctcccg gcctccagag atccgagagg aggaggttca gacggtggag       1800
gacggcgtgt tgacatcca cttgtaa                                            1827
```

<210> SEQ ID NO 20
<211> LENGTH: 608
<212> TYPE: PRT
<213> ORGANISM: Bos taurus

<400> SEQUENCE: 20

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
            20                  25                  30

Pro Gln Leu Val Arg Met Phe Leu Met Met His Pro Trp Tyr Ile Pro
        35                  40                  45

Ser Ser Gln Leu Ala Ala Lys Leu Leu His Ile Tyr Gln Gln Ser Arg
    50                  55                  60

```
Lys Asp Asn Ser Ser Ser Leu Gln Val Lys Thr Cys His Leu Val Arg
 65                  70                  75                  80

Tyr Trp Ile Ser Ala Phe Pro Ala Glu Phe Asp Leu Asn Pro Glu Leu
                 85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Glu Asn Val Pro Thr Tyr Lys
            115                 120                 125

Trp Lys Arg Gln Val Thr Gln Arg Asn Pro Val Glu Gln Lys Lys Arg
130                 135                 140

Lys Met Ser Leu Leu Phe Asp His Leu Glu Pro Leu Glu Leu Ala Ala
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
            195                 200                 205

Leu Met Ile Leu Ser Lys Pro Thr Ala Pro Gln Arg Ala Gly Val Ile
210                 215                 220

Thr His Phe Val His Val Ala Glu Glu Leu Leu His Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Pro Glu Thr Ile Lys Leu
            260                 265                 270

Trp Glu Gly Leu Thr Glu Leu Val Thr Ala Thr Gly Asn Tyr Gly Asn
            275                 280                 285

Tyr Arg Arg Arg Leu Ala Ala Cys Val Gly Phe Arg Phe Pro Ile Leu
290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Met Val Ser Leu
            355                 360                 365

Asp Gln Tyr Gln Thr Glu Asp Glu Leu Tyr Gln Leu Ser Leu Gln Arg
370                 375                 380

Glu Pro Arg Ser Lys Ser Ser Pro Thr Ser Pro Thr Thr Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Ile Met Val Glu His Ile Glu Lys Met Val Glu
            420                 425                 430

Ser Val Phe Arg Asn Phe Asp Val Asp Gly Asp Gly His Ile Ser Gln
            435                 440                 445

Glu Glu Phe Gln Ile Ile Arg Gly Asn Phe Pro Tyr Leu Ser Ala Phe
450                 455                 460

Gly Asp Leu Asp Gln Asn Gln Asp Gly Cys Ile Ser Lys Glu Glu Met
465                 470                 475                 480
```

```
Val Ser Tyr Phe Leu Arg Ser Ser Met Leu Gly Arg Met Gly
            485                 490                 495

Phe Val His Asn Phe His Glu Ser Asn Ser Leu Arg Pro Val Ala Cys
            500                 505                 510

Arg His Cys Lys Ala Leu Ile Leu Gly Ile Tyr Lys Gln Gly Leu Lys
            515                 520                 525

Cys Arg Ala Cys Gly Val Asn Cys His Lys Gln Cys Lys Asp Arg Leu
        530                 535                 540

Ser Val Glu Cys Arg Arg Ala Gln Ser Met Ser Leu Glu Gly Ser
545                 550                 555                 560

Ala Pro Ser Pro Ser Pro Thr His Thr His Arg Ala Phe Ser Phe
            565                 570                 575

Ser Leu Pro Arg Pro Gly Arg Arg Gly Ser Arg Pro Glu Ile Arg
            580                 585                 590

Glu Glu Glu Val Gln Thr Val Glu Asp Gly Val Phe Asp Ile His Leu
            595                 600                 605

<210> SEQ ID NO 21
<211> LENGTH: 608
<212> TYPE: PRT
<213> ORGANISM: Bos taurus

<400> SEQUENCE: 21

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
            20                  25                  30

Pro Gln Leu Val Arg Met Phe Leu Met Met His Pro Trp Tyr Ile Pro
            35                  40                  45

Ser Ser Gln Leu Ala Ala Lys Leu Leu His Ile Tyr Gln Gln Ser Arg
        50                  55                  60

Lys Asp Asn Ser Ser Ser Leu Gln Val Lys Thr Cys His Leu Val Arg
65                  70                  75                  80

Tyr Trp Ile Ser Ala Phe Pro Ala Glu Phe Asp Leu Asn Pro Glu Leu
                85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Glu Asn Val Pro Thr Tyr Lys
        115                 120                 125

Trp Lys Arg Gln Val Thr Gln Arg Asn Pro Val Glu Gln Lys Lys Arg
    130                 135                 140

Lys Met Ser Leu Leu Phe Asp His Leu Glu Pro Leu Glu Leu Ala Ala
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Pro Gln Arg Ala Gly Val Ile
    210                 215                 220

Thr His Phe Val His Val Ala Glu Glu Pro Leu His Leu Gln Asn Phe
225                 230                 235                 240

Asn Thr Leu Met Ala Val Val Gly Gly Leu Ser His Ser Ser Ile Ser
                245                 250                 255
```

Arg Leu Lys Glu Thr His Ser His Val Ser Pro Glu Thr Ile Lys Leu
                260                 265                 270

Trp Glu Gly Leu Thr Glu Leu Val Thr Ala Thr Gly Asn Tyr Gly Asn
            275                 280                 285

Tyr Arg Arg Arg Leu Ala Ala Cys Val Gly Phe Arg Phe Pro Ile Leu
        290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Met Val Ser Leu
        355                 360                 365

Asp Gln Tyr Gln Thr Glu Asp Glu Leu Tyr Gln Leu Ser Leu Gln Arg
370                 375                 380

Glu Pro Arg Ser Lys Ser Ser Pro Thr Ser Pro Thr Thr Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Ile Met Val Glu His Ile Glu Lys Met Val Glu
            420                 425                 430

Ser Val Phe Arg Asn Phe Asp Val Asp Gly Asp Gly His Ile Ser Gln
        435                 440                 445

Glu Glu Phe Gln Ile Ile Arg Gly Asn Phe Pro Tyr Leu Ser Ala Phe
        450                 455                 460

Gly Asp Leu Asp Gln Asn Gln Asp Gly Cys Ile Ser Lys Glu Glu Met
465                 470                 475                 480

Val Ser Tyr Phe Leu Arg Ser Ser Ser Met Leu Gly Gly Arg Met Gly
                485                 490                 495

Phe Val His Asn Phe His Glu Ser Asn Ser Leu Arg Pro Val Ala Cys
            500                 505                 510

Arg His Cys Lys Ala Leu Ile Leu Gly Ile Tyr Lys Gln Gly Leu Lys
        515                 520                 525

Cys Arg Ala Cys Gly Val Asn Cys His Lys Gln Cys Lys Asp Arg Leu
        530                 535                 540

Ser Val Glu Cys Arg Arg Arg Ala Gln Ser Met Ser Leu Glu Gly Ser
545                 550                 555                 560

Ala Pro Ser Pro Ser Pro Thr His Thr His His Arg Ala Phe Ser Phe
                565                 570                 575

Ser Leu Pro Arg Pro Gly Arg Arg Gly Ser Arg Pro Glu Ile Arg
            580                 585                 590

Glu Glu Glu Val Gln Thr Val Glu Asp Gly Val Phe Asp Ile His Leu
        595                 600                 605

<210> SEQ ID NO 22
<211> LENGTH: 608
<212> TYPE: PRT
<213> ORGANISM: Bos taurus

<400> SEQUENCE: 22

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
            20                  25                  30

-continued

```
Pro Gln Leu Val Arg Met Phe Leu Met Met His Pro Trp Tyr Ile Pro
             35                  40                  45

Ser Ser Gln Leu Ala Ala Lys Leu Leu His Ile Tyr Gln Gln Ser Arg
 50                  55                  60

Lys Asp Asn Ser Ser Ser Leu Gln Val Lys Thr Cys His Leu Val Arg
 65                  70                  75                  80

Tyr Trp Ile Ser Ala Phe Pro Ala Glu Phe Asp Leu Asn Pro Glu Leu
                 85                  90                  95

Ala Glu Gln Ile Lys Glu Leu Lys Ala Leu Leu Asp Gln Glu Gly Asn
             100                 105                 110

Arg Arg His Ser Ser Leu Ile Asp Ile Glu Asn Val Pro Thr Tyr Lys
         115                 120                 125

Trp Lys Arg Gln Val Thr Gln Arg Asn Pro Val Glu Gln Lys Lys Arg
     130                 135                 140

Lys Met Ser Leu Leu Phe Asp His Leu Glu Pro Leu Glu Leu Ala Ala
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Leu Gln Arg Ala Gly Val Ile
    210                 215                 220

Thr His Phe Val His Val Ala Glu Glu Leu Leu His Leu Gln Asn Phe
225                 230                 235                 240

Asn Thr Leu Met Ala Val Val Gly Gly Leu Ser His Ser Ser Ile Ser
                245                 250                 255

Arg Leu Lys Glu Thr His Ser His Val Ser Pro Glu Thr Ile Lys Leu
            260                 265                 270

Trp Glu Gly Leu Thr Glu Leu Val Thr Ala Thr Gly Asn Tyr Gly Asn
        275                 280                 285

Tyr Arg Arg Arg Leu Ala Ala Cys Val Gly Phe Arg Phe Pro Ile Leu
    290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Met Val Ser Leu
        355                 360                 365

Asp Gln Tyr Gln Thr Glu Asp Glu Leu Tyr Gln Leu Ser Leu Gln Arg
    370                 375                 380

Glu Pro Arg Ser Lys Ser Ser Pro Thr Ser Pro Thr Thr Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Ile Met Val Glu His Ile Glu Lys Met Val Glu
            420                 425                 430

Ser Val Phe Arg Asn Phe Asp Val Asp Gly Asp Gly His Ile Ser Gln
        435                 440                 445
```

```
Glu Glu Phe Gln Ile Ile Arg Gly Asn Phe Pro Tyr Leu Ser Ala Phe
    450                 455                 460

Gly Asp Leu Asp Gln Asn Gln Asp Gly Cys Ile Ser Lys Glu Glu Met
465                 470                 475                 480

Val Ser Tyr Phe Leu Arg Ser Ser Met Leu Gly Gly Arg Met Gly
                485                 490                 495

Phe Val His Asn Phe His Glu Ser Asn Ser Leu Arg Pro Val Ala Cys
                500                 505                 510

Arg His Cys Lys Ala Leu Ile Leu Gly Ile Tyr Lys Gln Gly Leu Lys
            515                 520                 525

Cys Arg Ala Cys Gly Val Asn Cys His Lys Gln Cys Lys Asp Arg Leu
            530                 535                 540

Ser Val Glu Cys Arg Arg Ala Gln Ser Met Ser Leu Glu Gly Ser
545                 550                 555                 560

Ala Pro Ser Pro Ser Pro Thr His Thr His His Arg Ala Phe Ser Phe
                565                 570                 575

Ser Leu Pro Arg Pro Gly Arg Arg Gly Ser Arg Pro Glu Ile Arg
                580                 585                 590

Glu Glu Glu Val Gln Thr Val Glu Asp Gly Val Phe Asp Ile His Leu
            595                 600                 605
```

```
<210> SEQ ID NO 23
<211> LENGTH: 608
<212> TYPE: PRT
<213> ORGANISM: Bos taurus

<400> SEQUENCE: 23

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
                20                  25                  30

Pro Gln Leu Val Arg Met Phe Leu Met Met His Pro Trp Tyr Ile Pro
            35                  40                  45

Ser Ser Gln Leu Ala Ala Lys Leu Leu His Ile Tyr Gln Gln Ser Arg
    50                  55                  60

Lys Asp Asn Ser Ser Ser Leu Gln Val Lys Thr Cys His Leu Val Arg
65                  70                  75                  80

Tyr Trp Ile Ser Ala Phe Pro Ala Glu Phe Asp Leu Asn Pro Glu Leu
                85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Glu Asn Val Pro Thr Tyr Lys
        115                 120                 125

Trp Lys Arg Gln Val Thr Gln Arg Asn Pro Val Glu Gln Lys Lys Arg
    130                 135                 140

Lys Met Ser Leu Leu Phe Asp His Leu Glu Pro Leu Glu Leu Ala Ala
145                 150                 155                 160

His Leu Thr Tyr Leu Glu Tyr Arg Ser Phe Cys Lys Ile Leu Phe Gln
                165                 170                 175

Asp Tyr His Ser Phe Val Thr His Gly Cys Thr Val Asp Asn Pro Val
            180                 185                 190

Leu Glu Arg Phe Ile Ser Leu Phe Asn Ser Val Ser Gln Trp Val Gln
        195                 200                 205

Leu Met Ile Leu Ser Lys Pro Thr Ala Leu Gln Arg Ala Gly Val Ile
    210                 215                 220
```

Thr His Phe Val His Val Ala Glu Glu Pro Leu His Leu Gln Asn Phe
225                 230                 235                 240

Asn Thr Leu Met Ala Val Val Gly Gly Leu Ser His Ser Ser Ile Ser
            245                 250                 255

Arg Leu Lys Glu Thr His Ser His Val Ser Pro Glu Thr Ile Lys Leu
        260                 265                 270

Trp Glu Gly Leu Thr Glu Leu Val Thr Ala Thr Gly Asn Tyr Gly Asn
    275                 280                 285

Tyr Arg Arg Arg Leu Ala Ala Cys Val Gly Phe Arg Phe Pro Ile Leu
290                 295                 300

Gly Val His Leu Lys Asp Leu Val Ala Leu Gln Leu Ala Leu Pro Asp
305                 310                 315                 320

Trp Leu Asp Pro Ala Arg Thr Arg Leu Asn Gly Ala Lys Met Lys Gln
                325                 330                 335

Leu Phe Ser Ile Leu Glu Glu Leu Ala Met Val Thr Ser Leu Arg Pro
            340                 345                 350

Pro Val Gln Ala Asn Pro Asp Leu Leu Ser Leu Leu Met Val Ser Leu
        355                 360                 365

Asp Gln Tyr Gln Thr Glu Asp Glu Leu Tyr Gln Leu Ser Leu Gln Arg
    370                 375                 380

Glu Pro Arg Ser Lys Ser Ser Pro Thr Ser Pro Thr Thr Cys Thr Pro
385                 390                 395                 400

Pro Pro Arg Pro Pro Val Leu Glu Glu Trp Thr Ser Ala Ala Lys Pro
                405                 410                 415

Lys Leu Asp Gln Ala Ile Met Val Glu His Ile Glu Lys Met Val Glu
            420                 425                 430

Ser Val Phe Arg Asn Phe Asp Val Asp Gly Asp Gly His Ile Ser Gln
        435                 440                 445

Glu Glu Phe Gln Ile Ile Arg Gly Asn Phe Pro Tyr Leu Ser Ala Phe
    450                 455                 460

Gly Asp Leu Asp Gln Asn Gln Asp Gly Cys Ile Ser Lys Glu Glu Met
465                 470                 475                 480

Val Ser Tyr Phe Leu Arg Ser Ser Ser Met Leu Gly Gly Arg Met Gly
                485                 490                 495

Phe Val His Asn Phe His Glu Ser Asn Ser Leu Arg Pro Val Ala Cys
            500                 505                 510

Arg His Cys Lys Ala Leu Ile Leu Gly Ile Tyr Lys Gln Gly Leu Lys
        515                 520                 525

Cys Arg Ala Cys Gly Val Asn Cys His Lys Gln Cys Lys Asp Arg Leu
    530                 535                 540

Ser Val Glu Cys Arg Arg Arg Ala Gln Ser Met Ser Leu Glu Gly Ser
545                 550                 555                 560

Ala Pro Ser Pro Ser Pro Thr His Thr His His Arg Ala Phe Ser Phe
                565                 570                 575

Ser Leu Pro Arg Pro Gly Arg Arg Gly Ser Arg Pro Glu Ile Arg
            580                 585                 590

Glu Glu Glu Val Gln Thr Val Glu Asp Gly Val Phe Asp Ile His Leu
        595                 600                 605

<210> SEQ ID NO 24
<211> LENGTH: 10
<212> TYPE: DNA
<213> ORGANISM: Bos taurus

<400> SEQUENCE: 24
cagaggaacc                                                                      10

<210> SEQ ID NO 25
<211> LENGTH: 10
<212> TYPE: DNA
<213> ORGANISM: Bos taurus

<400> SEQUENCE: 25
aggtgcaggg                                                                      10

<210> SEQ ID NO 26
<211> LENGTH: 24
<212> TYPE: PRT
<213> ORGANISM: Canis familiaris

<400> SEQUENCE: 26

Phe Asp His Leu Glu Pro Leu Glu Leu Ala Glu His Leu Thr Tyr Leu
1               5                   10                  15

Glu Tyr Arg Ser Phe Cys Lys Ile
            20

<210> SEQ ID NO 27
<211> LENGTH: 43
<212> TYPE: PRT
<213> ORGANISM: Canis familiaris

<400> SEQUENCE: 27

Arg Ala Leu Val Ile Thr His Phe Val His Val Ala Glu Lys Leu Leu
1               5                   10                  15

His Leu Gln Asn Phe Asn Thr Leu Met Ala Val Val Gly Gly Leu Ser
            20                  25                  30

His Ser Ser Ile Ser Arg Leu Lys Glu Thr His
        35                  40

<210> SEQ ID NO 28
<211> LENGTH: 23
<212> TYPE: PRT
<213> ORGANISM: Canis familiaris

<400> SEQUENCE: 28

Gly Phe Arg Phe Pro Ile Leu Gly Val His Leu Lys Asp Leu Val Ala
1               5                   10                  15

Leu Gln Leu Ala Leu Pro Asp
            20

<210> SEQ ID NO 29
<211> LENGTH: 6
<212> TYPE: PRT
<213> ORGANISM: Canis familiaris

<400> SEQUENCE: 29

Arg Leu Asn Gly Ala Lys
1               5

<210> SEQ ID NO 30
<211> LENGTH: 11
<212> TYPE: PRT
<213> ORGANISM: Canis familiaris

<400> SEQUENCE: 30

Leu Tyr Gln Leu Ser Leu Gln Arg Glu Pro Arg
1               5                   10

<210> SEQ ID NO 31
<211> LENGTH: 102
<212> TYPE: DNA
<213> ORGANISM: Canis familiaris

<400> SEQUENCE: 31

```
atggcgggcg ctctggacct ggacaagggc tgcatcgaag ccttcggtga aaacgtgcca    60
cctggtcagg tactggatct cagcattccc agcagagttt ga                       102
```

<210> SEQ ID NO 32
<211> LENGTH: 33
<212> TYPE: PRT
<213> ORGANISM: Canis familiaris

<400> SEQUENCE: 32

```
Met Ala Gly Ala Leu Asp Leu Asp Lys Gly Cys Ile Glu Ala Phe Gly
1               5                   10                  15

Glu Asn Val Pro Pro Gly Gln Val Leu Asp Leu Ser Ile Pro Ser Arg
            20                  25                  30

Val
```

<210> SEQ ID NO 33
<211> LENGTH: 17
<212> TYPE: DNA
<213> ORGANISM: Canis familiaris

<400> SEQUENCE: 33

```
tttttttttt cttttttt                                                  17
```

<210> SEQ ID NO 34
<211> LENGTH: 14
<212> TYPE: DNA
<213> ORGANISM: Canis familiaris

<400> SEQUENCE: 34

```
gggggggggga gggc                                                     14
```

<210> SEQ ID NO 35
<211> LENGTH: 16
<212> TYPE: DNA
<213> ORGANISM: Canis familiaris

<400> SEQUENCE: 35

```
ggtggtggtg gggggg                                                    16
```

<210> SEQ ID NO 36
<211> LENGTH: 23
<212> TYPE: PRT
<213> ORGANISM: Canis familiaris

<400> SEQUENCE: 36

```
Ser Phe Phe Leu Lys Asn Thr Asn Asp Gly Phe Glu Pro Phe Pro Leu
1               5                   10                  15

Glu Glu Asp Glu Glu Lys Asn
            20
```

<210> SEQ ID NO 37
<211> LENGTH: 23
<212> TYPE: PRT
<213> ORGANISM: Canis familiaris

```
<400> SEQUENCE: 37

Thr Phe Arg Gly Ala Pro Ser Asn Ser Phe Glu Glu Phe Pro Leu Ser
1               5                   10                  15

Ala Ile Glu Gly Trp Thr Glu
            20

<210> SEQ ID NO 38
<211> LENGTH: 23
<212> TYPE: PRT
<213> ORGANISM: Canis familiaris

<400> SEQUENCE: 38

Ser Phe Pro Gly Gln Pro Trp Ala Asn Asn Ser Asp Ile Leu Glu Ile
1               5                   10                  15

Pro Glu Ser Ser Arg Ala Leu
            20

<210> SEQ ID NO 39
<211> LENGTH: 6
<212> TYPE: PRT
<213> ORGANISM: Artificial
<220> FEATURE:
<223> OTHER INFORMATION: Platelet-activation peptide

<400> SEQUENCE: 39

Ser Phe Leu Leu Arg Asn
1               5

<210> SEQ ID NO 40
<211> LENGTH: 6
<212> TYPE: PRT
<213> ORGANISM: Artificial
<220> FEATURE:
<223> OTHER INFORMATION: Platelet-activation peptide

<400> SEQUENCE: 40

Ser Phe Phe Leu Lys Asn
1               5

<210> SEQ ID NO 41
<211> LENGTH: 22
<212> TYPE: PRT
<213> ORGANISM: Bos taurus

<400> SEQUENCE: 41

Gly Thr Cys Cys Cys Cys Cys Ala Gly Gly Ala Ala Cys Thr Cys Cys
1               5                   10                  15

Thr Gly Cys Ala Cys Cys
            20

<210> SEQ ID NO 42
<211> LENGTH: 22
<212> TYPE: PRT
<213> ORGANISM: Bos taurus

<400> SEQUENCE: 42

Gly Thr Cys Cys Cys Cys Cys Ala Gly Gly Ala Ala Cys Cys Cys Cys
1               5                   10                  15

Thr Gly Cys Ala Cys Cys
            20
```